United States Patent
Kapur et al.

(10) Patent No.: US 10,703,820 B2
(45) Date of Patent: Jul. 7, 2020

(54) METHODS AND COMPOSITIONS FOR REDUCING CARDIAC DAMAGE AND OTHER CONDITIONS

(71) Applicant: Tufts Medical Center, Inc., Boston, MA (US)

(72) Inventors: Navin K. Kapur, Hanover, MA (US); Richard H. Karas, Franklin, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 16/255,521

(22) Filed: Jan. 23, 2019

(65) Prior Publication Data

US 2019/0270825 A1 Sep. 5, 2019

Related U.S. Application Data

(63) Continuation of application No. 15/022,663, filed as application No. PCT/US2014/056313 on Sep. 18, 2014, now Pat. No. 10,214,590.

(60) Provisional application No. 61/880,551, filed on Sep. 20, 2013.

(51) Int. Cl.
| | | |
|---|---|---|
| *C12N 15/113* | (2010.01) |
| *C07K 16/28* | (2006.01) |
| *A61K 45/06* | (2006.01) |
| *A61K 38/17* | (2006.01) |
| *A61K 38/20* | (2006.01) |
| *A61K 38/21* | (2006.01) |
| *A61K 38/28* | (2006.01) |
| *A61K 38/48* | (2006.01) |
| *A61P 9/00* | (2006.01) |
| *A61K 39/395* | (2006.01) |
| *A61K 39/00* | (2006.01) |

(52) U.S. Cl.
CPC ........ *C07K 16/2896* (2013.01); *A61K 38/177* (2013.01); *A61K 38/1793* (2013.01); *A61K 38/2066* (2013.01); *A61K 38/21* (2013.01); *A61K 38/28* (2013.01); *A61K 38/4886* (2013.01); *A61K 39/3955* (2013.01); *A61K 45/06* (2013.01); *A61P 9/00* (2018.01); *C12Y 304/2408* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | |
|---|---|---|
| 8,221,753 B2 | 7/2012 | Theuer et al. |
| 9,468,666 B2 | 10/2016 | Kapur et al. |
| 2007/0077310 A1 | 4/2007 | Zemel et al. |
| 2008/0195327 A1 | 8/2008 | Young |
| 2009/0170767 A1 | 7/2009 | Karumanchi et al. |
| 2009/0286271 A1 | 11/2009 | Karumanchi et al. |
| 2010/0292300 A1 | 11/2010 | Van De Water et al. |
| 2011/0076263 A1 | 3/2011 | Theuer et al. |
| 2011/0129551 A1 | 6/2011 | Hubel et al. |
| 2014/0234319 A1 | 8/2014 | Kapur et al. |

FOREIGN PATENT DOCUMENTS

| | | |
|---|---|---|
| CN | 103781798 A | 5/2014 |
| WO | WO-02/072824 A2 | 9/2002 |
| WO | WO-2008/024300 A1 | 2/2008 |
| WO | WO-2011/088047 A1 | 7/2011 |
| WO | WO-2012/145539 A1 | 10/2012 |
| WO | WO-2013/019805 A1 | 2/2013 |

OTHER PUBLICATIONS

Dolinsek T, Markelc B, Sersa G, Coer A, Stimac M, et al. (2013) Multiple Delivery of siRNA against Endoglin into Murine Mammary Adenocarcinoma Prevents Angiogenesis and Delays Tumor Growth. PLoS One 8(3): e58723. doi:10.1371/journal.pone. 0058723. (Year: 2013).*

Extended European Search Report for 12820719.8, dated Mar. 17, 2015 (11 pages).

International Preliminary Report on Patentability for International Application No. PCT/US2014/056313, dated Mar. 22, 2016 (10 pages).

International Preliminary Report on Patentability for PCT/US2012/049018, dated Feb. 4, 2014 (6 pages).

International Search Report and Written Opinion for International Application No. PCT/US12/49018, dated Nov. 26, 2012 (15 pages).

International Search Report and Written Opinion for International Application No. PCT/US2014/056313, dated Dec. 31, 2014 (13 pages).

Jiang et al., "Abstract 4828: Effect of atorvastatin on pulmonary hypertension and lung function and remodeling in heart failure," Circulation. 118:S945 (2008).

(Continued)

*Primary Examiner* — Jennifer Pitrak McDonald
(74) *Attorney, Agent, or Firm* — Clark & Elbing LLP

(57) ABSTRACT

Endoglin has been identified to play a functional role as a regulator of TGFβ1 signaling, particular in TGFβ1-mediated calcineurin expression. The present invention features methods of reducing cardiac damage, particularly in a subject undergoing chemotherapy or radiation therapy by administering a composition that inhibits endoglin activity. The present invention also features methods of treating autoimmune diseases, inflammatory diseases, organ transplantation, and conditions association with oxidative stress related to TGFβ1-mediated calcineurin expression and reactive oxygen species (ROS) production by administering a composition that inhibits endoglin activity. The present invention also features methods of treating fibrotic diseases by administering a composition that inhibits endoglin activity.

10 Claims, 32 Drawing Sheets

Specification includes a Sequence Listing.

(56) References Cited

OTHER PUBLICATIONS

Kapur et al., "Abstract 1: Opposing roles for endoglin and soluble endoglin in cardiac remodeling and heart failure," Presented at AHA BCVS Meeting Jul. 20, 2011. Abstract Published in Circulation Research. 109: A1 (2011).

Kapur et al., "Reducing endoglin activity limits calcineurin and TRPC-6 expression and improves survival in a mouse model of right ventricular pressure overload," J Am Heart Assoc. 3(4):1-16 (2014) (17 pages).

Kapur, "Osler, Weber, and Rendu: Providing insights into cardiac remodeling a century later," Hematology Reports, 9th International Hereditary Hemorrhagic Telanglectasia Scientific Conference, May 20-24, Kemer, Antalya, Turkey. 3(2s): 29 (2011) (abstract only) (2 pages).

Kumar et al., "Antibody-directed coupling of endoglin and MMP-14 is a key mechanism for endoglin shedding and deregulation of TGF-beta signaling" Oncogene. 33(30):3970-9 (2014).

Notice of Reasons for Rejection for Japanese Patent Application No. 2014-524031, dated Apr. 25, 2016 (12 pages).

Office Action for Chinese Patent Application No. 201280048253.5, dated Jun. 2, 2015 (18 pages).

Oxenkrug, "Genetic and hormonal regulation of tryptophan-kynurenine metabolislm: Implications for vascular cognitive impairment, major depressive disorder, and aging," Ann N.Y. Acad Sci. 1122:35-49 (2007).

Pardali et al., "TGFbeta signaling and cardiovascular diseases," Int J Biol Sci. 8(2):195-213 (2012).

Shyu et al., "Mechanism of the inhibitory effect of atorvastatin on endoglin expression induced by transforming growth factor-beta1 in cultured cardiac fibroblasts," Eur J Heart Fail. 12(13):219-226 (2010).

Susman, "How can heart failure from chemotherapy be prevented?" Oncology Times. 2(11):21 (2005).

Wernig et al., "Unifying mechanism for different fibrotic diseases," Proc Natl Acad Sci USA. 114(18):4757-4762 (2017).

Wichers et al., "The role of indoleamine 2,3-dioxygenase (IDO) in the pathophysiology of interferon-alpha-induced depression," J Psychiatry Neurosci. 29(1):11-7 (2004).

Kapur et al., "Reduced endoglin activity limits cardiac fibrosis and improves survival in heart failure," Circulation. 125(22):2728-38 (including supplement) (2012) (19 pages).

Leask et al., "Dysregulation of transforming growth factor beta signaling in scleroderma: overexpression of endoglin in cutaneous scleroderma fibroblasts," Arthritis Rheum. 46(7):1857-65 (2002).

Burke et al., "Endoglin negatively regulates transforming growth factor beta1-induced profibrotic responses in intestinal fibroblasts," Br J Surg. 97(6):892-901 (2010).

Extended European Search Report for European Patent Application No. 18213558.2, dated Jul. 26, 2019 (10 pages).

* cited by examiner

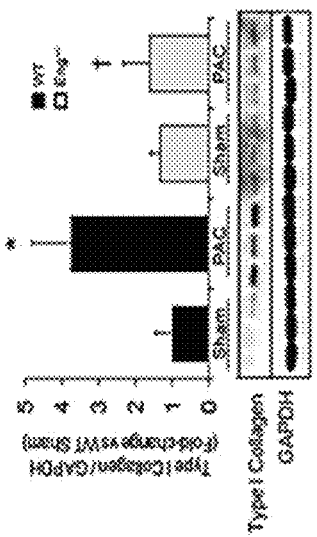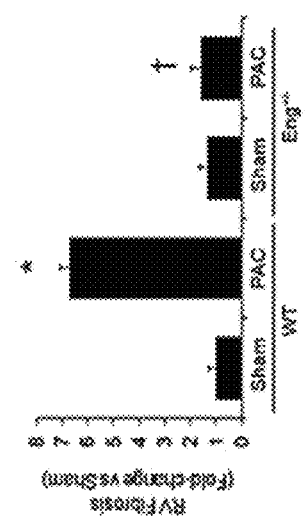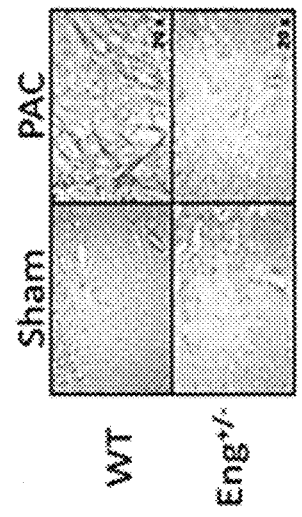

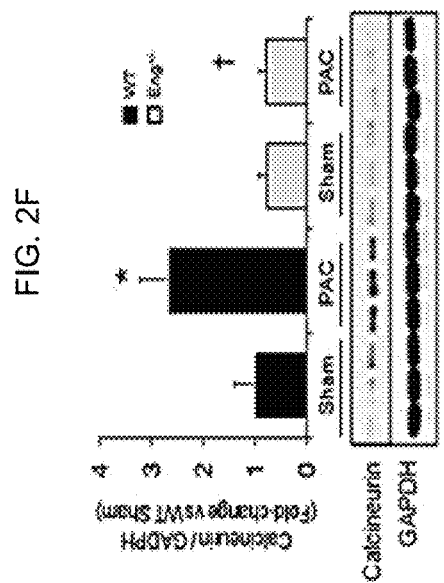
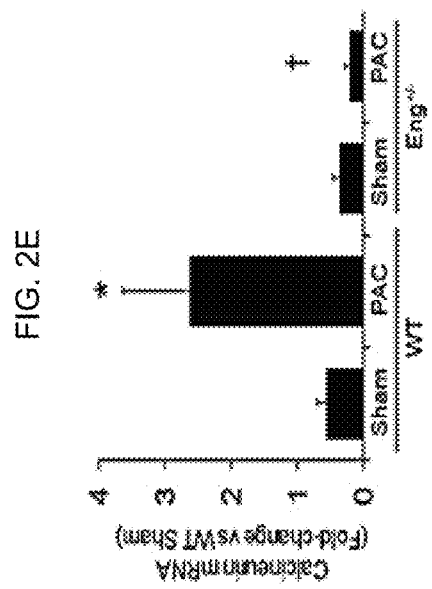
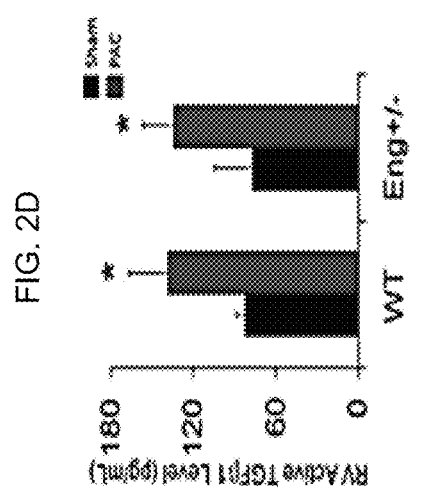

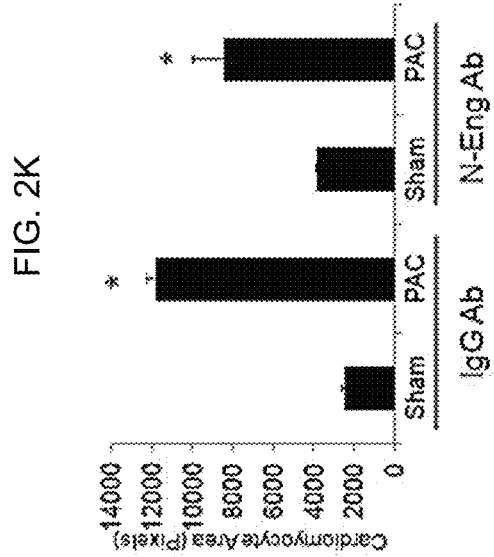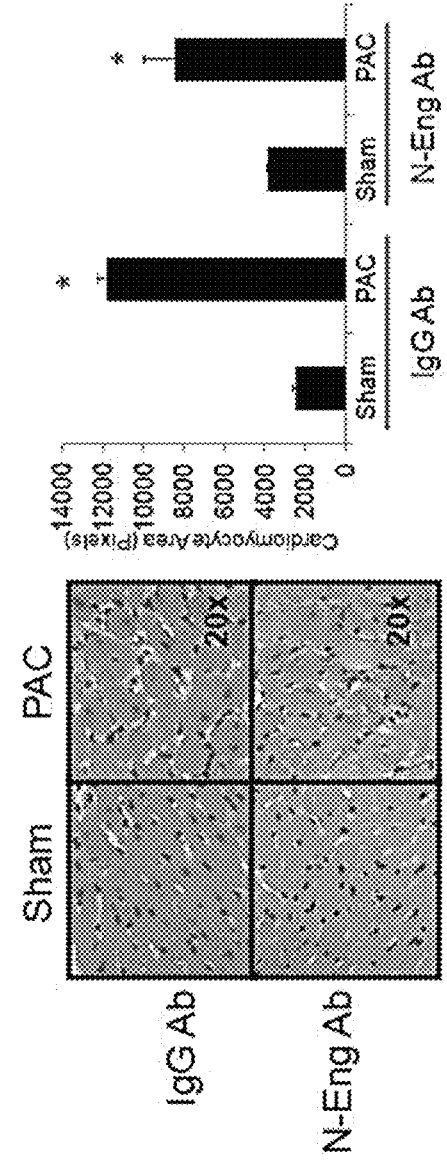

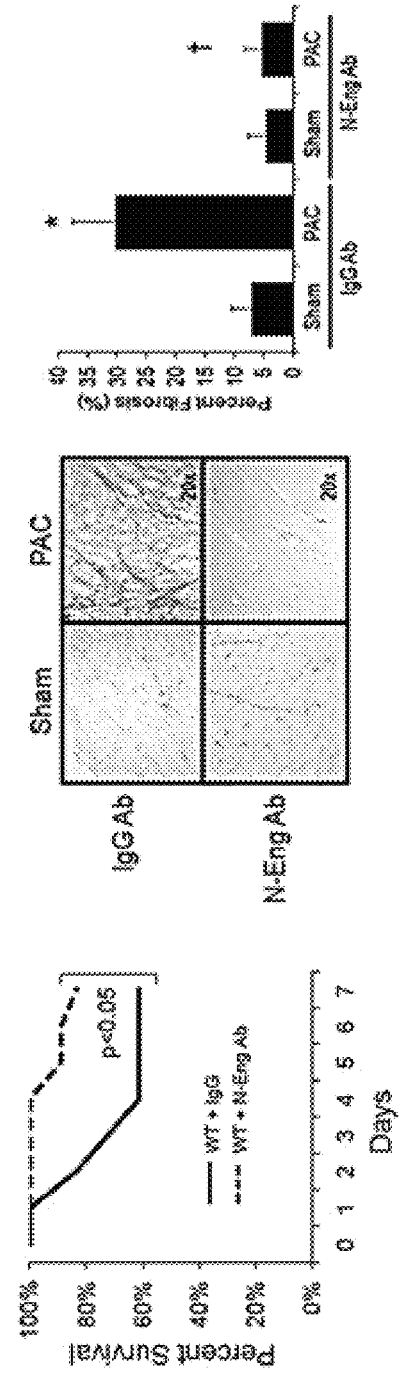

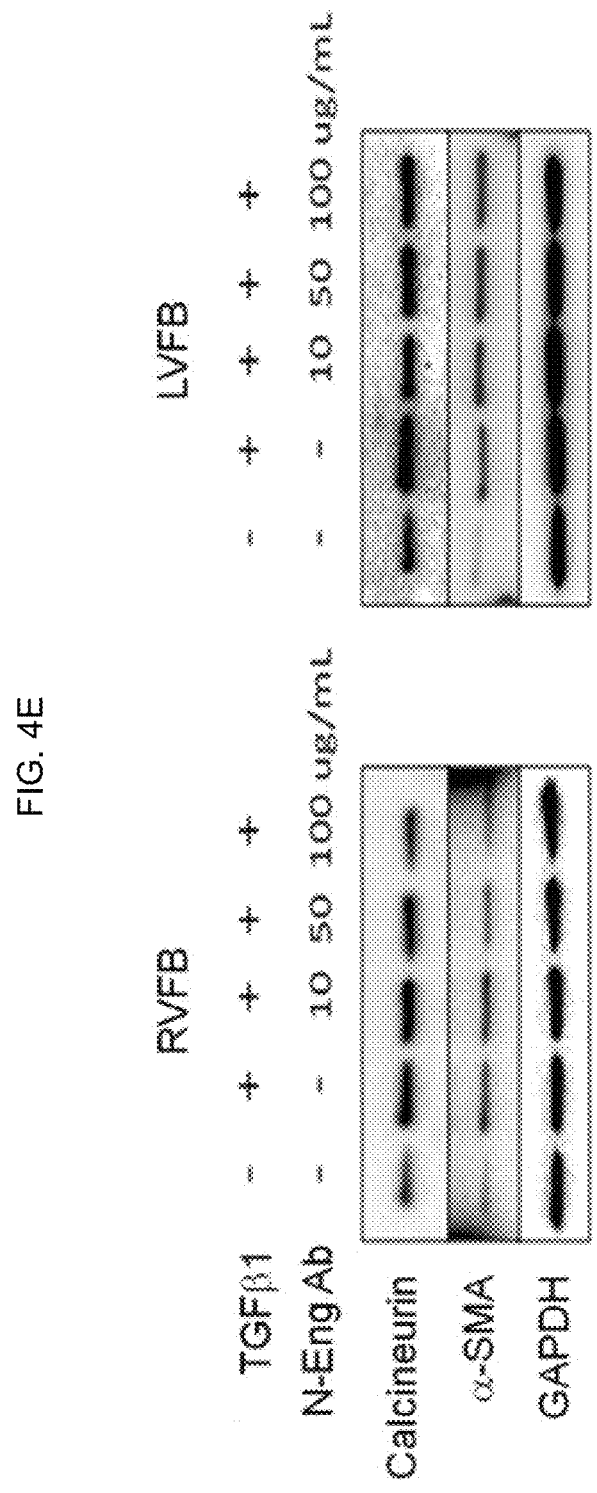

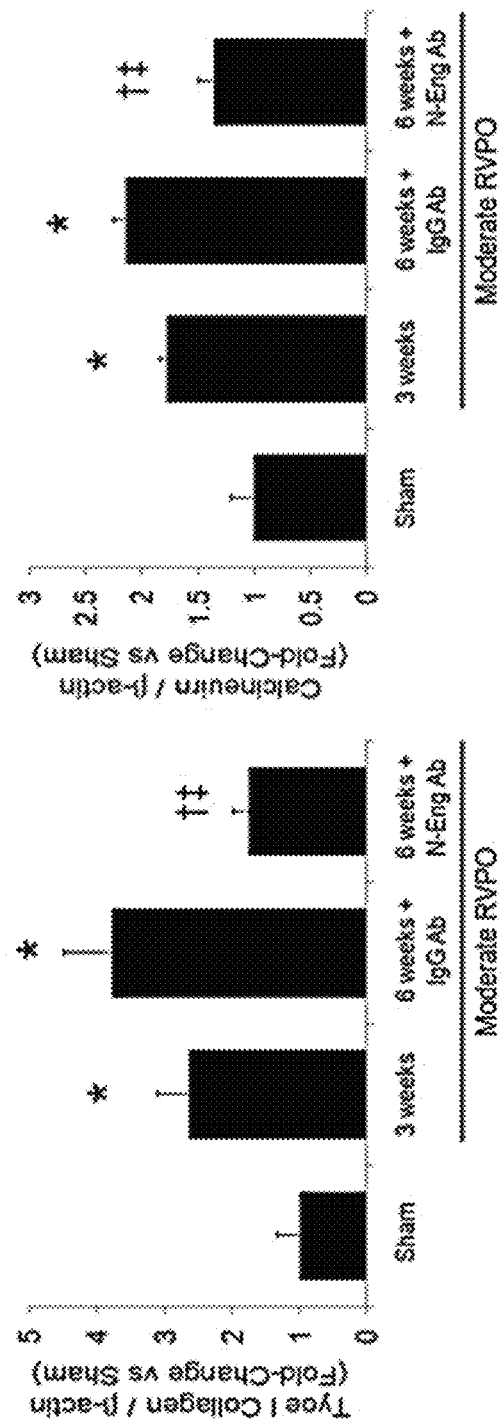

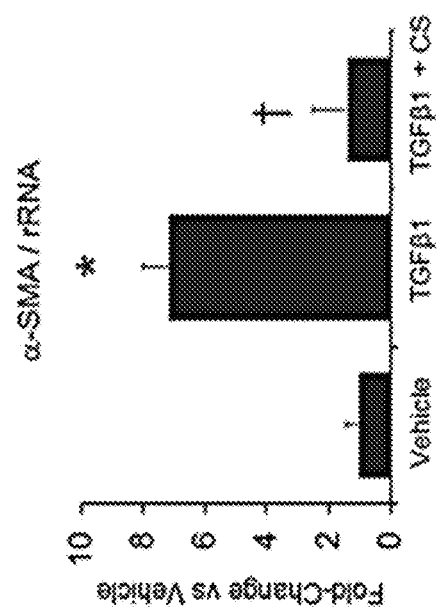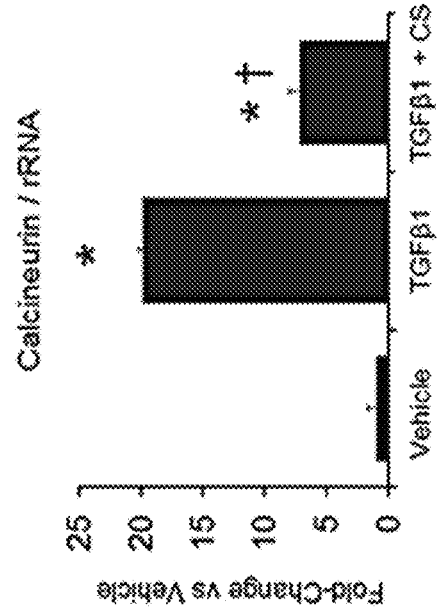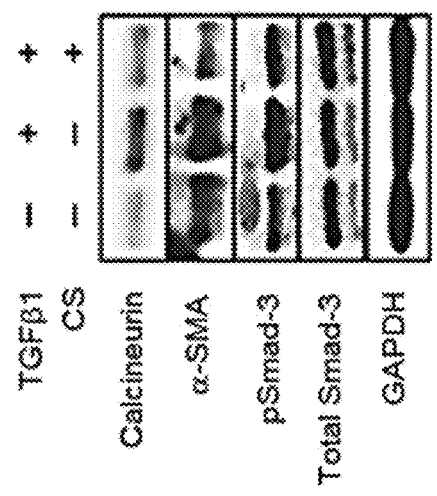

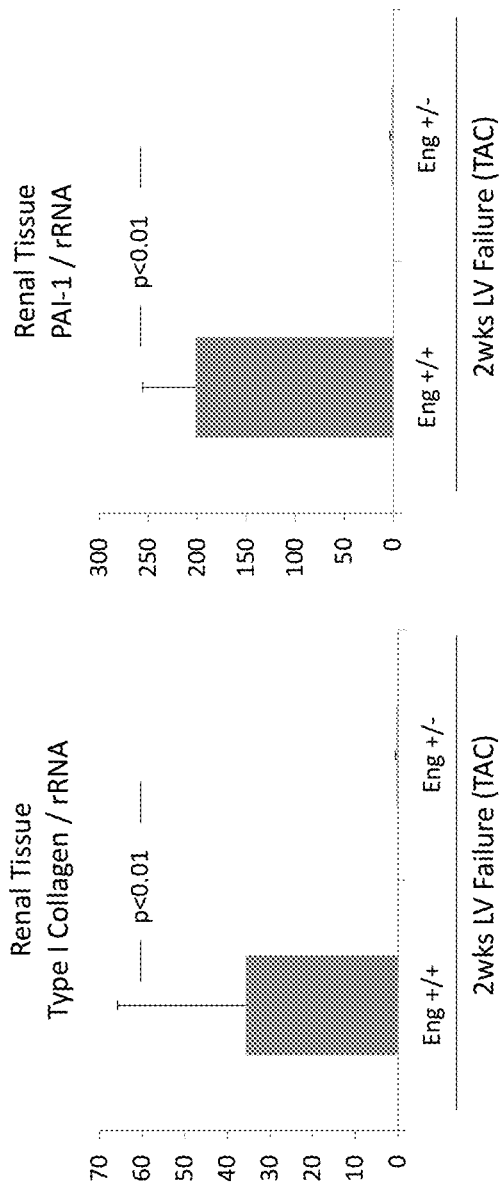

METHODS AND COMPOSITIONS FOR REDUCING CARDIAC DAMAGE AND OTHER CONDITIONS

CROSS-REFERENCE TO RELATED APPLICATIONS

This application is a continuation of, and claims priority to, U.S. patent application Ser. No. 15/022,663, now U.S. Pat. No. 10,214,590, filed Mar. 17, 2016, which is a National State Entry of International Patent Application No. PCT/US2014/056313, filed Sep. 18, 2014, which claims priority to U.S. Patent Application No. 61/880,551, filed Sep. 20, 2013, the contents of which are hereby incorporated by reference in their entirety.

GOVERNMENT LICENSE RIGHTS

This invention was made with government support under grant HL094909 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 13, 2019, is named 00398-536003_Sequence_Listing_5.13.19_ST25 and is 10,829 bytes in size.

BACKGROUND OF THE INVENTION

This invention relates to methods of reducing cardiac damage, particularly cardiac damage as a result of chemotherapy or radiation therapy. The invention also relates to the treatment of autoimmune diseases, fibrosis, inflammatory diseases, organ transplantation, and conditions associated with oxidative stress.

Right ventricular (RV) failure is a major determinant of morbidity and mortality for millions of individuals worldwide who suffer from lung disease or heart failure (McLaughlin et al., *J Am Coll Cardiol.* 53:1573-1619, 2009, Haddad et al., *Circ Heart Fail.* 4:692-699, 2011). RV failure is commonly a direct consequence of RV pressure overload (RVPO). Recent data confirms that elevated pulmonary artery systolic pressures are inversely associated with RV ejection fraction and directly related to increased mortality in both lung disease and left heart failure (Benza et al., *Circulation.* 122:164-172, 2010, Bursi et al. *J Am Coll Cardiol.* 59:222-231, 2012).

TGFβ1 is a powerful cytokine that governs cardiac fibrosis and signals through a heteromeric receptor complex comprised of a Type II ligand-binding receptor, a Type I activin-like kinase signaling receptors, and Type III accessory receptors, including endoglin. Upon activation, this receptor complex phosphorylates downstream effector proteins known as Smads (canonical pathway) or mitogen activated protein kinases (noncanonical pathway), including extracellular regulated kinase (ERK) (Leask, *Cardiovasc Res.* 74:207-212, 2007, Massague, *Annu Rev Biochem.* 67:753-791, 1998). Specifically, TGFβ1-induced phosphorylation of Smads-2/3 and ERK promotes Type I collagen synthesis and fibroblast proliferation (Kuwahara et al., *Circulation.* 106:130-135, 2002).

The calcium-dependent serine/threonine phosphatase, calcineurin, is another critical mediator of maladaptive cardiac remodeling, defined by excessive fibrosis and hypertrophy. Studies have shown that calcineurin increases expression of the canonical transient receptor protein channel 6 (TRPC-6), which triggers calcium influx and subsequent calcineurin activation, thereby setting up a self-propagating mechanism for pathologic hypertrophy, fibrosis, and increased mortality in heart failure. Noncanonical TGFβ1 signaling through TRPC-6 was reported to be an important stimulus for calcineurin-mediated alpha-smooth muscle cell active (α-SMA) expression, a marker of myofibroblast transformation and a critical component of cardiac fibrosis.

While it was recently reported that reduced endoglin expression limits left ventricular (LV) fibrosis and improves survival in a murine model of LV failure (Kapur et al., *Circulation.* 125:2728-2738, 2012), less is known about the functional role for endoglin in the RV and generally in organ fibrosis. Accordingly, there is a need to develop new targets for promoting RV cardiac remodeling for the treatment of heart failure. There is also a need to develop new targets for reducing organ fibrosis, such as, lung disease, and kidney disease, as well as new therapeutic approaches to prevent organ, heart, and other fibrosis related morbidity and mortality.

SUMMARY OF THE INVENTION

As described in detail below, endoglin was shown to be a central component of fibrogenic signaling in the RV and a positive regulator of TGFβ1-induced calcineurin/TRP expression. Given the importance of calcineurin in adaptive and maladaptive cardiac remodeling, targeting endoglin will result in reduced cardiac damage and improved survival. Furthermore, as endoglin was shown to modulate fibrotic signaling through the TGFβ1 pathway, a major signaling pathway in the initiation and progression of fibrogenesis, targeting endoglin provides a therapeutic approach for treatment of fibrotic diseases and prevention of fibrosis related morbidity and mortality. The inventors have discovered that reducing expression or activity of the membrane-bound receptor form of endoglin limits TGFβ1 signaling, not only in the heart, but in other organs (e.g., lung and kidney), thus resulting in a method for reducing organ fibrosis and improving survival.

Accordingly, in a first aspect, the invention features a method of reducing cardiac damage in a subject undergoing chemotherapy or radiation therapy, the method including administering to the subject a therapeutically effective amount of a composition that inhibits endoglin activity, wherein administration of the composition is begun prior to or concurrently with the start of chemotherapy or radiation therapy or following the development of chemotherapy- or radiation therapy-induced heart disease or heart failure. The composition may include an antibody, an antigen-binding fragment thereof, an RNAi agent, or a soluble polypeptide. In one embodiment, the antibody or antigen-binding fragment specifically inhibits endoglin activity or the antibody or antigen-binding fragment is an antagonist of the endoglin receptor. In a second embodiment, the polypeptide includes the amino acid sequence of soluble endoglin or an endoglin signaling-inhibitory fragment or analog thereof. In a third embodiment, the polypeptide is a protease, where the protease is matrix metalloproteinase 14 (MMP-14), an active fragment thereof, or includes an amino acid sequence having at least 80% identity to the amino acid sequence of MMP-14 having protease activity.

In particular embodiments, administration of the composition reduces, repairs, or remodels cardiac damage. In other embodiments, administration of the composition results in a reduction, repairing, or remodeling of cardiac fibrosis, ventricular hypertrophy, or improvement in blood vessel growth. In particular aspects, the reduction, repairing, or remodeling of cardiac damage in the subject is measured by an improvement in a cardiovascular parameter compared to a subject undergoing chemotherapy alone, where the cardiovascular parameter is selected form the group consisting of: end-diastolic volume, end-systolic volume, stroke volume, ejection fraction, heart rate, and cardiac output. In yet another embodiment, administration of the composition results in reduced levels of reactive oxygen species (ROS), reduction of TRP expression and/or activity, reduction of α-SMA expression and/or activity, or reduction of calcineurin expression and/or activity. Preferably, administration of the composition results in reduction of expression of one or more members of the TRP family, such as, TRPC, TRPM, or TRPV expression (e.g., TRPC-6, TRPM3, or TRPV2 expression). In another embodiment, the chemotherapy includes administration of a chemotherapeutic agent selected from the group consisting of: an alkylating agent, an anthracycline, an epothilone, a histone deacetylase inhibitor, an inhibitor of topoisomerase I, an inhibitor of topoisomerase II, a cytoskeletal disruptor, a kinase inhibitor, a monoclonal antibody, a peptide antibiotic, a nucleotide analog/precursor analog, a platinum-based agent, a retinoid, and a vinca alkaloid.

In another aspect, the invention features a method of treating or treating prophylactically a subject having an autoimmune disease, having a non-autoimmune inflammatory disease, or having undergone organ transplantation, the method including administering to the subject a therapeutically effective amount of a composition that inhibits endoglin activity. In certain embodiments, the composition is administered in addition to an immunosuppressive agent. In other embodiments, the composition is administered prior to administration of the immunosuppressive agent. In yet another aspect, the invention features a method of treating a condition associated with oxidative stress in a subject in need thereof, the method including administering to the subject a therapeutically effective amount of a composition that inhibits endoglin activity. In certain embodiments, the composition is administered in combination with a second agent, where the second agent is an anticancer/antiproliferative drug, a cardiovascular drug, or an anti-neurodegenerative drug. In other embodiments, the condition associated with oxidative stress is selected from the group consisting of: reperfusion injury, wound healing, toxic hepatitis, viral hepatitis, cirrhosis, chronic hepatitis, idiopathic pulmonary fibrosis, chronic lung disease, oxidative stress from dialysis, renal toxicity, kidney failure, ulcerative colitis, bacterial infection, viral infections, upper respiratory tract diseases, organ fibrosis, skin fibrosis, scleroderma, oxidative stress due to sun damage, and cancer. In particular embodiments, the condition associated with oxidative stress is a chronic condition. In some embodiments, the chronic condition is chronic organ disease, selected from the group consisting of: chronic lung disease, chronic obstructive pulmonary disease, chronic viral hepatitis, chronic renal disease, chronic pancreatitis, chronic prostatitis, chronic inherited bleeding disorders, and chronic bone disease. In certain aspects, the administration of the composition reduces the levels of reactive oxygen species (ROS).

In a final aspect, the invention features a method of treating a fibrotic disease in a subject in need thereof, the method including administering to the subject a therapeutically effective amount of a composition that inhibits endoglin activity. In some embodiments, the fibrotic disease is selected from the group consisting of idiopathic pulmonary fibrosis, organ fibrosis, interstitial lung disease, skin fibrosis, diabetic nephropathy, liver fibrosis, liver cirrhosis, nonalcoholic steatohepatitis (NASH), rheumatoid arthritis, fibrosarcomas, keloids and hypertrophic scars, arteriosclerosis, kidney disease, macular degeneration, retinal and vitreal retinopathy, surgical complications, chemotherapeutic drug-induced fibrosis, radiation-induced fibrosis, accidental injury, burns, local scleroderma, and systemic scleroderma. Preferably, the fibrotic disease is idiopathic pulmonary fibrosis. In some embodiments, the composition is administered with an antifibrotic agent, selected from the group consisting of: pentoxyphiline, tocopherol, vitamin E, pioglitazone, INT 747, peginterferon 2b, infliximab, ribavirin, glycyrrhizin, candesartan, losartan, irbesartan, ambrisentan, FG-3019, warfarin, insulin, colchicines, peginterferon 2a, etanercept, pirfenidone, nintedanib, and IL-10. In particular embodiments, administration of the composition reduces the levels of ROS, collagen expression, or promotes tissue remodeling.

In all embodiments of the invention, the composition that inhibits endoglin signaling is formulated for oral, parenteral, cutaneous, subcutaneous, topical, transdermal, ocular administration, or by injection, inhalation, or direct contact with the nasal or oral mucosa. In other embodiments of all of the above inventions, the composition inhibits TGFβ1-mediated endoglin activity or calcineurin-mediated endoglin activity. In yet another embodiment of the above inventions, the administration of the composition further provides cardiac protection in the subject.

Definitions

By "administration prior to" is meant administration of a composition of the invention in a therapeutically effective amount before the start of chemotherapy or radiation therapy (e.g., 4 weeks prior, 3 weeks prior, 2 weeks prior, 1 week prior, 6 days prior, 5 days prior, 4 days prior, 3 days prior, 2 days prior, 1 day prior, less than 24 hours prior (e.g., less than 23, 20, 19, 18, 17, 16, 15, 10, 9, 8, 7, 6, 5, 4, 3, 2 hours, or 1 hour) to the start of chemotherapy or radiation therapy.

By "administration concurrently with" is meant administration of a composition of the invention in a therapeutically effective amount with the start of chemotherapy or radiation therapy (e.g., less than 2, 6, 12, 18, or 24 hours after the start of chemotherapy or radiation therapy. Alternatively, "administration concurrently with" can mean between the first and second doses of chemotherapy or radiation therapy.

By "chemotherapy" is meant treatment of a disease by administering an agent (e.g., a small molecule, an antibody, or an antigen-binding fragment thereof) that reduces or reverses the growth of cancer cells (e.g., destroys cancerous tissue).

By "chronic" is meant the state of human health condition or disease that is persistent or otherwise long-lasting in its effects (e.g., course of condition or disease that last for more than three months). Chronic conditions or diseases often lead to morbidity and/or mortality. Examples of chronic conditions and diseases include but are not limited to cancer, blindness, Alzheimer's disease, Parkinson's disease, deafness, mental illness, chronic pain syndromes, and those described herein, for example, chronic lung disease, chronic obstructive pulmonary disease, chronic viral hepatitis, chronic renal disease, chronic pancreatitis, chronic prostatitis, chronic inherited bleeding disorders, or chronic bone disease.

By "subject" is meant a human or non-human animal (e.g., a mammal).

By "soluble endoglin" is meant a polypeptide that includes the extracellular domain of endoglin, but does not include the transmembrane or cytoplasmic domains of endoglin and has the ability to decrease TGFβ1-mediated activation of the endoglin receptor.

By "soluble endoglin fragment" is meant a fragment of at least 4, 5, 6, 8, 10, 15, 20, 25, 30, 40, 50, 60, 70, 80, 100, 125, 150, 175, 200, 225, 250, 300, 350, 400, or 450 amino acids of soluble endoglin.

By "at least 80% identity" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "at least 80% identical" to a reference sequence has at least 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence of or reducing the severity of a disease, disorder or condition by administering a therapeutic agent to the subject prior to the onset of disease symptoms.

Other features and advantages of the invention will be apparent from the following Detailed Description, the drawings, and the claims.

BRIEF DESCRIPTION OF THE DRAWINGS

FIGS. 1A-1B show levels of endoglin mRNA and protein expression in WT and Eng+/− mice after PAC (n=6/group). FIG. 1C shows Kaplan-Meier survival curves in WT and Eng+/− mice after PAC (n=12/group). FIG. 1D shows right ventricular systolic pressure in WT and Eng+/− mice after PAC (n=6/group). FIG. 1E shows right ventricular stroke volume in WT and Eng+/− mice after PAC (n=6/group). FIG. 1F shows total body weight in WT and Eng+/− mice after PAC (n=6/group). *, $p<0.05$ vs Sham; †, $p<0.05$ vs WT vs. Eng+/− sham, ‡, $p<0.05$ Wt vs. Eng+/−PAC. FIG. 1G show histologic staining (hematoxylin and eosin) of right ventricular (RV) cardiomyocytes in WT and Eng+/− mice after pulmonary artery constriction (PAC). FIG. 1H shows quantification of RV cardiomyocyte cross-sectional area. FIGS. 1I-1J show quantification of RV pSmad-3 and p-ERK1/2 protein levels in WT and Eng+/− after PAC. Representative western blots are shown below graphs (*, $p<0.05$ vs Sham; †, $p<0.05$ vs WT-PAC).

FIGS. 2A-2M show that reduced endoglin expression improves survival and limits calcineurin activity after right ventricular pressure overload. FIGS. 2A-2B show representative histologic staining for RV collagen abundance in WT and Eng+/− mice after PAC. Quantification of RV fibrosis after PAC is shown (n=6/group). FIG. 2C shows quantification of RV Type I collagen protein levels in WT and Eng+/− mice after PAC (n=6/group). A representative western blot is shown. FIG. 2D shows levels of active TGFβ1 in RV protein lysates from WT and Eng+/− mice (n=6/group). FIGS. 2E-2F show levels of RV calcineurin mRNA and protein in WT and Eng+/− mice after PAC (n=6/group). A representative western blot is shown. FIGS. 2G-2I show levels of RV MYH7, TRPC-6, and α-SMA mRNA expression in WT and Eng+/− mice after PAC (n=6/group). *, $p<0.05$ vs Sham; †, $p<0.05$ vs. WT-PAC. FIG. 2J shows histologic staining (hematoxylin and eosin) of right ventricular (RV) cardiomyocytes in WT mice treated with a N-Eng Ab or IgG Ab after pulmonary artery constriction (PAC). FIG. 2K shows quantification of RV cardiomyocyte cross-sectional area. FIGS. 2L-2M show quantification of RV pSmad-3 and p-ERK1/2 protein levels in WT mice treated with a N-Eng Ab or IgG Ab after PAC. Representative western blots are shown below graphs (*, $p<0.05$ vs Sham; †, $p<0.05$ vs. WT-PAC).

FIGS. 3A-3I show that neutralizing endoglin activity improves survival and limits the development of cardiac fibrosis after right ventricular pressure overload. FIG. 3A shows Kaplan-Meier survival curves in WT mice treated with an IgG control antibody or N-Eng Ab after PAC (n=18/group). FIGS. 3B-3C show representative histologic staining for RV collagen abundance in IgG versus N-Eng Ab treated mice after PAC. Quantification of RV fibrosis after PAC is shown (n=6/group). FIG. 3D shows quantification of RV Type I collagen protein levels in IgG versus N-Eng Ab treated mice after PAC (n=6/group). A representative western blot is shown. FIG. 3E shows quantification of RV calcineurin protein levels in IgG versus N-Eng Ab treated mice after PAC (n=6/group). A representative western blot is shown. FIGS. 3F-3H show levels of RV MYH7, TRPC-6, and α-SMA mRNA expression in IgG versus N-Eng Ab treated mice after PAC (n=6/group). *, $p<0.05$ vs. Sham; †, $p<0.05$ vs. WT+N-Eng Ab PAC. FIG. 3I is Western blots showing protein levels of pSmad-3 and pERK-1/2 in RVFB and LVFB stimulated with TGFb1 in the presence and absence of increasing concentrations of N-Eng Ab.

FIGS. 4A-4E show that reduced endoglin activity limits calcineurin expression and myofibroblast conversion in right ventricular fibroblasts. FIGS. 4A-4B show calcineurin and α-SMA mRNA levels in fibroblasts from the right (RVFB) and left (LVFB) ventricles of WT and Eng+/− mice before and after TGFβ1 stimulation. FIG. 4C is a set of representative western blots showing calcineurin-SMA levels after TGFβ1 stimulation in RVFB and LVFB from WT and Eng+/− mice. FIGS. 4D-4E show quantification of calcineurin and α-SMA protein levels in RVFB and LVFB stimulated with TGFβ1 in the presence and absence of increasing concentrations of N-Eng Ab. Representative western blots for calcineurin and α-SMA protein levels in RVFB and LVFB are shown.

FIGS. 5A-5E show that neutralizing endoglin activity reverses cardiac fibrosis after chronic right ventricular pressure overload. FIG. 5A shows a representative histologic staining for RV collagen abundance in IgG versus N-anti-Eng Ab treated mice after moderate RVPO. FIG. 5B shows quantification of RV fibrosis after moderate RVPO is shown (n=6/group). FIGS. 5C-5E are western blots showing levels of type I collagen and calcineurin in WT mice after moderate RVPO for 3 and 6 weeks in the presence and absence of either an IgG control antibody or N-Eng Ab. Quantification of Type I collagen and calcineurin protein levels. *, p<0.05 vs. Sham; †, p<0.05 vs. 3 weeks RVPO, ‡, p<0.05 vs. 6 weeks RVPO+IgG.

FIGS. 7A-7F show calcineurin regulates myofibroblast transformation and TRPC-6 expression in right ventricular fibroblasts. FIG. 7A is a Western blots showing calcineurin, α-SMA, pSmad3, total Smad3, and GAPDH expression in human right ventricular fibroblasts (RVFB) after stimulation with TGFβ1 (10 ng/mL for 16 to 24 hours) in the presence and absence of cyclosporine (CS). FIGS. 7B and 7D show mRNA levels of calcineurin, α-SMA, and TRPC-6 in human RVFB after stimulation with TGFβ1 in the presence and absence of CS (n=3/group). FIG. 7E is a Western blot showing silencing of TRPC-6 in human RVFB. FIG. 7F is a Western blot showing calcineurin and α-SMA levels in human RVFB after TGFβ1 stimulation in the presence and absence of a siRNA against TRPC-6 (siTRPC-6). *P<0.05 versus vehicle; †P<0.05 versus TGFβ1 stimulation; ‡P<0.05 versus WT+TGFβ1 stimulation. α-SMA indicates a-smooth muscle antigen; TGFβ1, transforming growth factor beta 1; TRPC-6, transient receptor protein channel 6.

FIGS. 8A-8C show RV systolic pressure, tau, and RV compliance in Eng+/+ and Eng+/− mice after 5 weeks of treatment with Sugen compound under normoxic (Su-Norm) or hypoxic (Su-Hypox) conditions (n=6/group). FIG. 8D shows mRNA levels of type I collagen in WT and Eng+/− mice under Su-Norm or Su-Hypox conditions (n=6/group). FIGS. 8E and 8F are representative histologic staining for RV collagen abundance in Eng+/+ and Eng+/− mice under Su-Norm or Su-Hypox conditions. Quantification of percent RV fibrosis is shown (n=6/group). FIG. 8G shows mRNA levels of calcineurin, TRPC-6, and α-SMA in RV tissue from WT and Eng+/− mice under Su-Norm or Su-Hypox conditions (n=6/group). *P<0.05 versus Eng+/+Su-Norm; †P<0.05 versus Eng+/−Su-Norm; ‡P<0.05 Eng+/+Su-Hypox versus Eng+/−Su-Hypox. α-SMA indicates a-smooth muscle antigen; RV, right ventricular; TRPC-6, transient receptor protein channel 6; WT, wild type.

FIGS. 14A-14B are graphs showing kidney type I collagen expression and plasminogen activator inhibitor-1 (PAI-1) expression in Eng+/+ and Eng+/− mice after two weeks of LV failure induced by TAC.

DETAILED DESCRIPTION

Figure 1A:
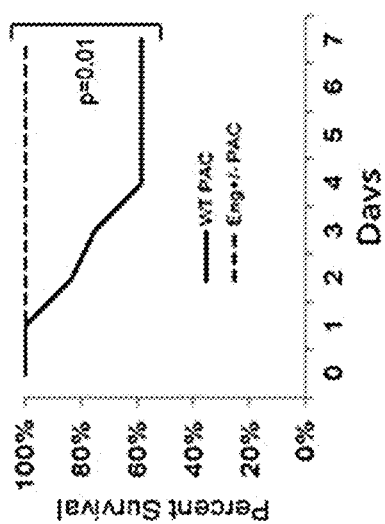
FIGS. 1A-1J show that reduced endoglin expression improves survival and limits calcineurin activity after right ventricular pressure overload.

Endoglin is an important participant in the biology of right ventricle (RV) remodeling and a potential therapeutic target that modulates TGFβ1 signaling, regulates calcineurin, and TRPC-6 expression. Several findings by the inventors, as described in detail below, have important clinical implications. Specifically, endoglin, as a central component of fibrogenic signaling in the RV, provides an important approach to reduce RV fibrosis and improve survival in RV pressure overload. Endoglin was also shown to be an important component in fibrogenic signaling in the lung and kidney. Further, endoglin was identified as a previously unrecognized positive regulator of calcineurin expression in vivo. It was further shown that blocking endoglin reduces RV calcineurin expression in models of acute and chronic RV pressure overload. In addition, endoglin specifically regulates TGFβ1-induced calcineurin expression and myofibroblast transformation in fibroblasts derived from the RV. It was also shown that endoglin regulates TRPC-6 expression in response to RV and LV pressure overload and that pressure overload induces distinct profiles of TRPC, TRPM, and TRPV expression in the RV and LV and the effects in the RV require full endoglin activity. Finally, the potential clinical utility of targeting endoglin was examined in mice with established RVPO by randomizing mice to a neutralizing antibody against endoglin or isotype control antibody. In this experiment, progressive fibrosis in the control arm and a reversal of established RV fibrosis in the anti-endoglin treatment group was observed. Given the importance of calcineurin/TRPC-6 in adaptive and maladaptive cardiac remodeling, these findings implicate an important role for endoglin in RV remodeling and further show that targeting endoglin activity may improve RV function in heart failure, lung disease, or kidney disease. In addition, given the importance of TGFβ signaling and its link with major profibrogenic signaling networks, these findings implicate an important role for endoglin in regulation of fibrogenesis and further show that targeting endoglin activity can provide a therapeutic approach to treating organ and tissue fibrosis.

Endoglin

Endoglin (Eng; CD105) is a 180 kDa membrane-associated dimeric glycoprotein (mEng) that is also found as a circulating form composed of the extracellular domain, known as soluble endoglin (sEng). Endoglin plays an important role in vascular remodeling. Under basal conditions the vascular endothelium responds to TGFβ1 through the TGF-β type II receptor in association with either of two type I signaling receptors known as activin like kinase (ALK)1 and ALK5, which promote either a proliferative or quiescent phenotype respectively. Endoglin modulates responses to TGFβ1 and is implicated in the regulation of the switch from ALK5 to ALK1 signaling pathways. It was previously reported that endoglin is a modulator of TGFβ1 signaling in cardiac fibroblasts and heart failure, where fibrosis plays a major role, however the role of endoglin in cardiac remodeling, specifically in the right ventricle has been largely unexplored.

Right Ventricle Cardiac Remodeling, TGFβ1 Signaling, Endoglin, Calcineurin, and TRP Signaling Previous studies of TGFβ1 activity in cardiac remodeling have been more focused on left ventricular failure. It was recently reported that reduced endoglin activity limits LV fibrosis by attenuating canonical and non-canonical TGFβ1 signaling in a murine model of left heart failure. In those studies, the effect of reduced endoglin activity on LV calcineurin expression was not observed. Several other studies have shown that both TGFβ1 and calcineurin play critical roles in regulating LV responses to injury (Kuwahara et al., Circulation. 106:130-135, 2002, Kapur et al., Circulation. 125:2728-2738, 2012, White et al., A. Ther Adv Cardiovasc Dis. 6:5-14, 2012, Fickenberg et al., Am J Pathol. 163:355-366, 2003, Davis et al., Dev Cell. 23:705-715, 2012, Heineke et al., J Mol Cell Cardiol. 48:1080-1087, 2010, Berry et al., Circ Res. 109:407-417, 2011); however, no studies have examined a functional interaction between TGFβ1 and calcineurin in RV remodeling. Here, a mouse model of pulmonary artery constriction was used to uncouple the RV from the pulmonary vasculature and to explore the direct impact of pressure overload on RV remodeling. It was first observed that RV endoglin expression is increased in response to RVPO and then it was shown that endoglin promotes RV fibrosis by facilitating TGFβ1 signaling through canonical and non-canonical pathways.

In both in vivo and in vitro studies, a neutralizing antibody to endoglin (N-Eng Ab, TRC105), which is an IgG1 antibody that binds both human and mouse endoglin with high avidity was used. TRC105 has been studied extensively in cancer biology and is known to bind and disrupt endoglin signaling in endothelium (Rosen et al., Clin Cancer Res. 18:4820-4829, 2012, Seon et al., Curr Drug Deliv. 8:135-143, 2011). It has been shown that TRC105 blocks endoglin activity in cardiac fibroblasts. To begin exploring the potential clinical utility of blocking endoglin as a treatment for adverse RV remodeling, a randomized study in WT mice subjected to moderate RVPO for 3 weeks then treated with either TRC105 or an isotype control IgG Ab for an additional 3 weeks was performed. After 6 weeks, progressive RV fibrosis in the control arm and reduced RV fibrosis in the anti-endoglin treated group was observed. Collectively, these findings confirm that targeting endoglin using an antibody mediated approach can prevent the development of RV fibrosis in acute RVPO and reverse established RV fibrosis in a chronic model of moderate RVPO.

To further explore the dependence of TGFβ1-induced calcineurin expression and myofibroblast transformation on endoglin, cardiac fibroblasts were studied in vitro. Using WT and Eng+/− mice, it was first identified that endoglin was required for TGFβ1-induced calcineurin expression and myofibroblast transformation in RV, but not LV fibroblasts. This observation was confirmed by blocking endoglin with the N-Eng Ab, TRC105, which also attenuated TGFβ1-induced calcineurin expression and myofibroblast transformation in RV, not LV fibroblasts. In both loss-of-function studies, it was observed that reducing endoglin activity limited phosphorylation of Smad-3 and ERK-1/2 in both RV and LV fibroblasts, thereby attenuating expression of type I collagen, suggesting that endoglin plays an important role in regulating biventricular TGFβ1 signaling with a potentially unique role for endoglin in the TGFβ1/calcineurin pathway that is specific to fibroblasts of RV origin.

Transient receptor potential (TRP) channels of multiple subclasses are expressed in the heart, including cardiomyocytes, fibroblasts, endothelial cells, and vascular smooth muscle cells (Nilius et al., Physiol Rev. 87:165-217, 2007; Watanabe et al., Pharmacol Ther. 118:337-351, 2008). TRP channels expressed in the heart most likely coordinate signaling within local domains or through direct interaction with $Ca^{2+}$-dependent regulatory proteins (Eder et al., Circ Res. 108:265-272, 2011). The TRPC subclass appears to regulate the cardiac hypertrophic response. In particular, TRPC3 and TRPC6 were implicated in angiotensin II-induced nuclear factor of activated T-cells (NFAT) activation in isolated cardiomyocytes (Onohara et al., EMBO J. 25:5305-5316, 2006), which is an essential step of cardiac hypertrophy development in the whole heart. The TRPM subclass, particularly TRPM4, has been proposed to generate a $Ca^{2+}$-activated nonselective $Ca^{2+}$ channel (NSCC) in atrial myocytes that might be responsible for delayed after-depolarizations (Guinamard et al., J Physiol. 558:75-83, 2004). Several TRPs have also been implicated in blood pressure regulation, among those are the TRPM4, TRPV1, TRPV4, TRPC1, and TRPC6 channels (Dietrich et al., Thromb Haemost. 103:262-270, 2005; Mathar et al., J Clin. Invest. 120:3267-3279, 2010; Willette et al., J Pharmacol Exp Ther. 326, 443-452, 2008; Pacher et al., J Physiol. 558:647-657, 2004; Suzuki et al., J Biol Chem 278.22664-22668, 2003).

To explore a functional role for endoglin as a regulator of TRPM, TRPV, and TRPC expression in response to RV or LV pressure overload, Eng+/−(endoglin haploinsufficient) and Eng+/+(wild-type) mice were exposed to thoracic aortic (TAC) or pulmonary arterial (PAC) construction for 10 weeks. Analysis of biventricular tissue by real-time polymerase chain reaction (RT-PCR) showed that pressure overload induced distinct profiles of TRPM, TRPV, and TRPC expression in the RV and LV of mice and the effects, particularly in the RV, require full endoglin activity. It was further shown that endoglin is necessary for TGFβ1 induced increase in expression of TRPC-6 and α-SMA by a calcineurin-dependent mechanism in human RV fibroblasts and that TRPC-6 mediates a feedback loop promoting calcineurin expression and myofibroblast transformation in human RV fibroblasts that is also dependent on endoglin. In Eng+/− mice exposed to Sugen+ hypoxia, reduced endoglin activity improved RV diastolic function, limited fibrosis, and attenuated expression of calcineurin, TRPC-6, and α-SMA. Taken together, the data support that endoglin is also an important regulator of TRP expression in modulating RV responses to injury.

TGFβ Signaling and Fibrosis

TGFβ belongs to Th1 cytokines and is synthesized by a wide variety of cells including macrophages, mononuclear cells, and fibroblasts. TGFβ1, TGFβ2, TGFβ3 form the TGFβ subfamily and their synthesis is cell type- and context-dependent with unique as well as similar functions. TGFβ is a major player in initiation and progression of fibrogenesis. In response to vascular injury, infiltrated mononuclear cells produce TGFβ and other growth factors in the wound area. As a chemo-attractant, TGFβ attracts neutrophils to the wound site and thus acts as an inflammatory cytokine in the initial stage of wound healing. TGFβ also induces migration of fibroblasts from the vicinity of wounds, and fibroblast to myofibroblasts differentiation. TGFβ-activated fibroblasts or differentiated myofibroblasts are the major cell-type that synthesizes collagen and other extracellular matrix proteins to heal the damaged tissues. Specifically, TGFβ1-induced phosphorylation of Smads-2/3 and ERK promotes Type I collagen synthesis and fibroblast proliferation. However, sustained activation of myofibroblasts, due to chronic inflammation and TGFβ signaling, leads to the development of fibrosis and eventually organ failure.

Given that the inventors previously reported that reduced endoglin activity limits LV fibrosis by attenuating canonical and non-canonical TGFβ1 signaling in a murine model of left heart failure it is an object of the present invention to investigate the role of endoglin in modulating fibrotic signaling via TGFβ1 signaling in other organs. To examine whether fibrotic signaling in other organ tissues is endoglin-dependent, type 1 collagen expression was analyzed in lung tissue and kidney tissue of Eng+/+ and Eng+/− mice. The results show that reduced endoglin expression attenuates increased collagen expression in lungs and kidneys, thus, indicating that endoglin is required for regulation of fibrotic signaling and modulation of endoglin activity would be useful in the context of tissue fibrosis.

Soluble Endoglin

The methods of the invention can, in certain embodiments, employ soluble endoglin, a soluble endoglin fragment, or a soluble endoglin analog, e.g., a fragment or an analog that retains the ability to bind TGFβ1.

Full length endoglin is a 180 kDa homodimeric co-receptor for members of the TGF-β superfamily. Two isoforms of endoglin are known: a 633 amino acid protein and 600 amino acid protein. These two forms differ in the length of their cytoplasmic tail; the longer form has 47 amino acid tail (L-mEng), whereas the shorter form has a 14 amino acid cytoplasmic tail (S-mEng). The amino acid sequences of endoglin are described in NCBI accession numbers NP_001108225 and NP_000109.1 and are shown in FIG. 10. The mature endoglin sequences include amino acids 26 to 658 of isoform 1 and amino acids 26-625 of isoform 2. In both isoforms, amino acids 587 to 611 are predicted to be the transmembrane domain. The corresponding extracellular region (amino acids 26 to 586 or 27 to 586) of endoglin, fragments thereof, or analogs thereof may therefore be used in the invention.

The methods described herein can also use a fragment of soluble endoglin (e.g., any of those described herein. Preferred fragments are capable of binding TGFβ1, e.g., with at least 1%, 5%, 10%, 15%, 20%, 25%, 35%, 50%, 75%, 80%, 85%, 90%, 95%, 97%, or 99% of the binding affinity of soluble endoglin or the naturally occurring form of soluble endoglin.

The methods described herein can also use a soluble endoglin analog. In certain embodiments, the analog has at least 60%, 70%, 80%, 85%, 90%, 95%, 96%, 97%, 98%, or 99% sequence identity to soluble endoglin or to a soluble endoglin fragment. Preferred analogs are capable of binding TGFβ1, e.g., with at least 1%, 5%, 10%, 15%, 20%, 25%, 35%, 50%, 75%, 80%, 85%, 90%, 95%, 97%, or 99% of the binding affinity of soluble endoglin.

Antibodies

The methods of the invention can employ an antibody that prevents endoglin activity or an antigen-binding fragment thereof. In certain embodiments, the antibody specifically binds to mEng or to sEng. The antibody can bind specifically to the extracellular domain (ECD) of mEng, the residual membrane-associated component of mEng after cleavage of the ECD, or to circulating sEng. The antibody can be a monoclonal or a polyclonal antibody. In certain embodiments, the antibody is humanized. The antibody or antibody fragment can be a single chain antibody (scFv), Fab, Fab'2, scFv, SMIP, diabody, nanobody, aptamer, or domain antibody.

Antibodies (e.g., monoclonal, polyclonal, poly-specific, or mono-specific antibodies) against endoglin (e.g., antagonistic antibodies) can be made using any of the numerous methods for making antibodies known in the art. In one example, the relevant endoglin sequence is produced as a C-terminal fusion with glutathione S-transferase (GST) (Smith et al., Gene 67:31-40, 1988). The fusion protein is purified on glutathione-Sepharose beads, eluted with glutathione, cleaved with thrombin (at an engineered cleavage site), and purified for immunization of rabbits. Primary immunizations are carried out with Freund's complete adjuvant and subsequent immunizations with Freund's incomplete adjuvant. Antibody titers are monitored by Western blot and immunoprecipitation analyses using the thrombin-cleaved protein fragment of the GST fusion protein. Immune sera are affinity purified using CNBr-Sepharose-coupled protein. Antiserum specificity can be determined using a panel of unrelated GST proteins.

Alternatively, monoclonal antibodies that specifically bind endoglin can be prepared using standard hybridoma technology (see, e.g., Kohler et al., Nature 256:495-7, 1975; Kohler et al., Eur. J. Immunol. 6:511-9, 1976; Kohler et al., Eur. J. Immunol. 6:292-5, 1976; Hammerling et al., Monoclonal Antibodies and T Cell Hybridomas, Elsevier, NY, 1981). Once produced, monoclonal antibodies can also be tested for specific recognition by Western blot or immunoprecipitation analysis. Alternatively, monoclonal antibodies can be prepared using the polypeptide of the invention described above and a phage display library (Vaughan et al., Nat. Biotechnol. 14:309-14, 1996).

In order to generate polyclonal antibodies on a large scale and at a low cost an appropriate animal species can be chosen. Polyclonal antibodies can be isolated from the milk or colostrum of, e.g., immunized cows. Bovine colostrum contains 28 g of IgG per liter, while bovine milk contains 1.5 g of IgG per liter (Ontsouka et al., J. Dairy Sci. 86:2005-11, 2003). Polyclonal antibodies can also be isolated from the yolk of eggs from immunized chickens (Sarker et al., J. Pediatr. Gastroenterol. Nutr. 32:19-25, 2001).

Useful antibodies can be identified in several different screening assays. First, antibodies are assayed by ELISA to determine whether they are specific for the immunizing antigen (i.e., endoglin).

Using standard techniques, ELISA plates are coated with immunogen, the antibody is added to the plate, washed, and the presence of bound antibody detected by using a second antibody specific for the Ig of the species in which the antibody was generated.

RNA Interference

The methods described herein can also use RNAi to inhibit endoglin expression. RNA interference (RNAi) is a mechanism of post-transcriptional gene silencing (PTGS) in which double-stranded RNA (dsRNA) corresponding to a gene or mRNA of interest is introduced into an organism, resulting in the degradation of the corresponding mRNA. In the RNAi reaction, both the sense and anti-sense strands of a dsRNA molecule are processed into small RNA fragments or segments ranging in length from 21 to 23 nucleotides (nt) and having 2-nucleotide 3' tails. Alternatively, synthetic dsRNAs, which are 21 to 23 nt in length and have 2-nucleotide 3' tails, can be synthesized, purified, and used in the reaction. These 21 to 23 nt dsRNAs are known as "guide RNAs" or "short interfering RNAs" (siRNAs).

The siRNA duplexes then bind to a nuclease complex composed of proteins that target and destroy endogenous mRNAs having homology to the siRNA within the complex. The complex functions by targeting the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene. siRNAs can also be chemically synthesized or obtained from a company that chemically synthesizes siRNAs (e.g., Dharmacon Research Inc., Pharmacia, or ABI). Endoglin RNAi molecules are commercially available and can be obtained from a variety of sources, including Santa Cruz Biotechnology (siRNA; Cat. No. sc-35302). The specific requirements and modifications of dsRNA are described in PCT Publication No. WO 01/75164, and in U.S. Patent Application Publication No. 20060067937 and PCT Publication No. WO 06/034507, incorporated herein by reference.

Small Molecule Inhibitors

Small molecule inhibitors of endoglin activity can be screened for using methods known in the art. High-throughput screening techniques can be used to identify candidate small molecules that modulate, alter, or decrease endoglin expression or biological activity (e.g., a decrease by at least 10%, 20%, 30%, 40%, 50%, 60%, 70%, 80%, 90%, 95% or more compared to a normal reference).

In particular examples, candidate small molecules having one or more of the following properties are considered inhibitors of endoglin activity: decrease endoglin expression, reduced TGFβ1 signaling, reduced phosphorylated Smad 2/3 and mitogen activated protein kinases (e.g., ERK), reduced calcineurin expression, or reduced reactive oxygen species (ROS) production, compared to a control or a normal reference. Candidate small molecules can be tested for their effect on endoglin activity using assays known in the art.

Candidate small molecules can also be tested for their effect on endoglin activity using any particular cell based assays described herein. Standard methods may be used to measure analyte levels or cellular parameters in any bodily fluid, including, but not limited to, urine, blood, serum, plasma, saliva, or cerebrospinal fluid. Such methods include immunoassay, ELISA, Western blotting using antibodies directed to endoglin and quantitative enzyme immunoassay techniques. ELISA assays are the preferred method for measuring polypeptide levels. Accordingly, the measurement of antibodies specific to endoglin in a subject may also be used to determine if a compound has effects on endoglin activity.

In one embodiment, a compound that affects endoglin activity may show a decrease in the expression of a nucleic acid encoding endoglin. Methods for detecting such alterations are standard in the art. In one example Northern blotting or real-time PCR is used to detect mRNA levels.

In another embodiment, hybridization techniques may be used to monitor expression levels of a gene encoding a polypeptide of the invention upon treatment with a candidate compound.

In a further embodiment, a reporter gene such as a gene encoding GFP or luciferase can be fused to the endoglin promoter to monitor the expression levels of endoglin upon treatment with a candidate compound.

In general, candidate compounds are identified from large libraries of both natural product or synthetic (or semi-synthetic) extracts, chemical libraries, according to methods known in the art. Those skilled in the field of drug discovery and development will understand that the precise source of test extracts or compounds is not critical to the screening procedure(s) of the invention.

Proteases

The compositions of the invention can include proteases, particularly matrix metalloproteinase 14 (MMP-14). MMP-14 (UniProtKB:P50281) is a known cleavage protease of the endoglin receptor. The advantages of protease cleavage of the endoglin receptor is that 1) cleavage of the endoglin receptor can be a companion diagnostic with soluble endoglin to measure the efficacy and identify optimal candidates for anti-endoglin therapy and 2) the release of soluble endoglin as a result of protease cleavage would provide feedback to further inhibit endoglin signaling thereby enhancing potency of the compositions described herein. In some embodiments, the composition can include a polypeptide having an amino acid sequence having at least 80% identity (e.g., at least 85%, 90%, 92%, 95%, 96%, 97%, 98%, or 99%) to the amino acid sequence of MMP-14 shown below and having protease activity.

```
                                             (SEQ ID NO: 1)
MSPAPRPPRCLLLPLLTLGTALASLGSAQSSSFSPEAWLQQYGYLPPGDL

RTHTQRSPQSLSAAIAAMQKFYGLQVTGKADADTMKAMRRPRCGVPDKFG

AEIKANVRRKRYAIQGLKWQHNEITFCIQNYTPKVGEYATYEAIRKAFRV

WESATPLRFREVPYAYIREGHEKQADIMIFFAEGFHGDSTPFDGEGGFLA

HAYFPGPNIGGDTHFDSAEPWTVRNEDLNGNDIFLVAVHELGHALGLEHS

SDPSAIMAPFYQWMDTENFVLPDDDRRGIQQLYGGESGFPTKMPPQPRTT

SRPSVPDKPKNPTYGPNICDGNFDTVAMLRGEMFVFKERWFWRVRNNQVM

DGYPMPIGQFWRGLPASINTAYERKDGKFVFFKGDKHWVFDEASLEPGYP

KHIKELGRGLPTDKIDAALFWMPNGKTYFFRGNKYYRFNEELRAVDSEYP

KNIKVWEGIPESPRGSFMGSDEVFTYFYKGNKYWKFNNQKLKVEPGYPKS

ALRDWMGCPSGGRPDEGTEEETEVIIIEVDEEGGGAVSAAAVVLPVLLLL

LVLAVGLAVFFFRRHGTPRRLLYCQRSLLDKV
```

MMP-14 belongs to a class of matrix metalloproteinases (MMPs) within the super family of zinc endopeptidases. The protease contains seven domains: a signal peptide leading MMP-14 into the secretory pathway, a propeptide domain maintaining MMP in a latent form, a catalytic domain responsible for enzymatic activity, a hinge region maintaining proper conformation, a hemopexin domain required for substrate reorganization, a transmembrane domain anchoring MMP into the plasma membrane, and a cytoplasmic domain required for endocytosis (Stocker et al., *Curr Opin Struct Biol.* 3:383-390, 1995, Knauper et al., *J Biol Chem.* 271:17124-17131, 1996).

The catalytic domain, or active fragment of MMP-14, is a highly conserved motif containing a methionine and three histidines that bind a zinc ion in the catalytic site. In some embodiments, the composition includes an active fragment of MMP-14, for example, an active fragment having at least 90% (e.g., at least 92%, 95%, 96%, 97%, 98%, or 99%) identity to the amino acid sequence below.

(SEQ ID NO: 2)
AIQGLKWQHNEITFCIQNYTPKVGEYATYEAIRKAFRVWESATPLRFREV
PYAYIREGHEKQADIMIFFAEGFHGDSTPFDGEGGFLAHAYFPGPNIGGD
THFDSAEPWTVRNEDLNGNDIFLVAVHELGHALGLEHSSDPSAIMAPFYQ
WMDTENFVLPDDDRRGIQQLYGGESG

Conditions

Chemotherapy and Radiation Therapy-Induced Cardiotoxicity

The observations that endoglin is a regulator of calcineurin expression in the RV and can serve as a novel therapeutic target to limit fibrosis and improve survival in RV pressure overload have important implications for RV failure in multiple clinical settings.

Anticancer therapies (e.g., chemotherapy) and radiation therapies have led to a long life expectancy for many patients; however treatment-related cardiac toxicity can be a side effect of anticancer therapies and radiation therapies that increases the mortality rate in these patients. The compositions of the invention, therefore, can be administered prior to or concurrently with the start of anticancer therapies or radiation therapies to provide cardioprotection and reduce the incidence of cardiac toxicity. Additionally, the compositions can be administered following the development of chemotherapy or radiation induced heart disease or heart failure. Furthermore, the dosing and timing for administration of the composition of the invention depends on different factors related to the type of chemotherapeutic agent, dose administered during each cycle, cumulative dose, schedule of administration, route of administration, combination of other cardiotoxic drugs or association with radiotherapy, age of the subject, presence of cardiovascular risk factors, or previous cardiovascular disease.

The composition can be administered in a therapeutically effective amount prior to the start of chemotherapy or radiation therapy (e.g., 4 weeks prior, 3 weeks prior, 2 weeks prior, 1 week prior, 6 days prior, 5 days prior, 4 days prior, 3 days prior, 2 days prior, 1 day prior, within less than 24 hours prior to the start of chemotherapy or radiation therapy). The administration of the composition of the invention can be continued throughout the duration of chemotherapy or radiation therapy and extends past the conclusion of chemotherapy or radiation therapy (e.g., extended 1 day, 2, days, 3 days, 4 days, 5 days, 1 week, 2 weeks, 3 weeks, 4 weeks, 5 weeks, 6 weeks after the conclusion of chemotherapy or radiation therapy). The composition can also be administered concurrently with the start of chemotherapy or radiation therapy (e.g., before 24 hours after the start of chemotherapy, administered daily, twice daily, every other day, every other week, and in doses of less than about 3 mg/kg (e.g., 2.9 mg/kg, 2.8 mg/kg, 2.7 mg/kg, 2.6 mg/kg, 2.5 mg/kg, 2.3 mg/kg, 2.2 mg/kg, 2.1 mg/kg, 2.0 mg/kg, 1.8 mg/kg, 1.7 mg/kg, 1.5 mg/kg, 1.2 mg/kg, 0.5 mg/kg, 0.3 mg/kg), or more than about 3.5 mg/kg (e.g., 3.6 mg/kg, 3.8 mg/kg, 4.0 mg/kg, 4.5 mg/kg, 5.0 mg/kg, 5.5 mg/kg, 6.0 mg/kg, 6.5 mg/kg, 7 mg/kg, 10 mg/kg, 15 mg/kg).

A reduction in cardiac damage can be quantitatively measured by an improvement in a cardiovascular parameter (e.g., end-diastolic volume (EDV), end-systolic volume (ESV), stroke volume, ejection fraction, heart rate, and cardiac output) when compared to normal ranges (e.g., an end-diastolic volume (EDV) from about 65-240 mL, an end-systolic volume (ESV) from about 16-143 mL, a stroke volume from about 55-100 mL, an ejection fraction from about 55-70%, a heart rate from about 60-100 bpm, and/or cardiac output of about 4.0-8.0 L/min).

Autoimmune Disease, Non-Autoimmune Inflammatory Diseases, Organ Transplantation

A previously unrecognized functional role for endoglin as a regulator of calcineurin signaling and myofibroblast transformation was observed. Using Eng+/− mice and WT mice treated with a neutralizing antibody against endoglin, an improved survival and a significant reduction in RV fibrosis compared to WT controls after 7 days of severe RVPO was observed. These findings confirmed an important role for endoglin in RV fibrosis; however the most dramatic observation was the complete loss of calcineurin expression in the pressure-overloaded RV and associated reduction in levels of genes upregulated by calcineurin, including MYH7 and TRPC-6. Consistent with the report from Davis et al. (Dev Cell. 23:705-715, 2012) implicating an important role for calcineurin/TRPC-6 as regulators of myofibroblast transformation, an association between reduced TRPC-6 and α-SMA levels in the RV was observed, suggesting a disruption of myofibroblast transformation despite increased tissue levels of active TGFβ1. These data identify endoglin as an essential component of RV remodeling and a potential therapeutic target that regulates calcineurin expression, reduces RV fibrosis, and improves survival in RV pressure overload.

The compositions of the invention can be used alone or in combination with inhibitors of the calcineurin pathway to treat autoimmune disease, non-autoimmune inflammatory disease, and/or organ transplantation. Examples of autoimmune disease and inflammatory diseases include, but are not limited to acne vulgaris, asthma, autoimmune diseases (e.g., acute disseminated encephalomyelitis (ADEM), Addison's disease, agammaglbulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmunehemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo concentric sclerosis, Behcet's disease, Berger's disease, Bickerstaff's encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic vasculitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, giant cell arteritis, glomerulonephritis, Goodpasture's syndrome, Grave's disease, Guillain-Barre syndrome, Hashimoto's encephalopathy, Hashimoto's thyroiditis, Henoch-Schonlein purpura, herpes gestationis, hidradenitis suppurativa, Hughes-Stovin syndrome, hypogammaglobulinemia, idiopathic inflammatory demyelinating diseases, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, lupus erythematosus, Majeed syndrome, Meniere's disease, microscopic polyangiitis, mixed connective tissue disease, morphea, Mucha-Habermann disease, myasthenia gravis, myositis, narcolepsy, neuromyelitis optica, neuromyotonia, ocular cicatricial pemphigoid, opsoclonus myoclonus syndrome, Ord's thyroiditis, palindromic rheumatism, PANDAS, paraneoplastic cerebellar degeneration, paroxysmal nocturnal hemoglobinuria, Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriatic arthritis, psoriasis, pyoderma gangrenosum, pure red cell aplasia, Rasmussen's encephalitis, raynaud phenomenon, relapsing polychondritis, Reiter's syndrome, restless leg syndrome, retroperitoneal fibrosis, rheumatic fever, Schnitzler syndrome, scleritis, scleroderma, serum sickness, Sjogren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, undifferentiated spondyloarthropathy, vitiligo, and Wegener's granulomatosis), celiac disease, chronic prostatitis, glomerulonephritis, hypersensitivities, inflammatory bowel diseases, pelvic inflammatory disease, reperfusion injury, sarcoidosis, transplant rejection, vasculitis, interstitial cystitis, and osteoarthritis.

The compositions of the invention are also expected to be effective in treating ischemia-reperfusion injury from reconstructive and organ transplantation procedures. Exemplary tissues and organs to be treated using the composition of the invention have active metabolism and increased mitochondrial function and are susceptible to reperfusion injury after brief periods of ischemia and include but are not limited to; skeletal muscle, the heart, the liver, large intestine, small intestine, the brain, the skin, the limbs (e.g., arms, legs, feet, hands).

Conditions Associated with Oxidative Stress

Reports have identified that TGFβ1 activates calcineurin expression and activity by generating reactive oxygen species (ROS), thus, impaired function of the TGFβ1 co-receptor, endoglin, should limit calcineurin expression and activity by reducing ROS. Accordingly, the composition of the invention can be used to treat conditions associated with oxidative stress related to increase ROS production. Examples of conditions associated with oxidative stress include, but are not limited to reperfusion injury, wound healing, toxic hepatitis, viral hepatitis, chronic organ disease (e.g., chronic lung disease, chronic obstructive pulmonary disease, chronic viral hepatitis, chronic renal disease, chronic pancreatitis, chronic prostatitis, chronic inherited bleeding disorders (e.g., hemophilia, von Willebrand disease), and chronic bone disease (e.g., osteogenesis imperfect, Paget's disease), oxidative stress from dialysis, renal toxicity, kidney failure, ulcerative colitis, bacterial infection, viral infections, upper respiratory tract diseases, oxidative stress due to sun damage, eczema, atopic dermatitis, polymyositis, and dermatitis herpetiformis.

Other conditions that may be treated using the compositions of the invention include cancers. Cancers are generally characterized by unregulated cell growth, formation of malignant tumors, and invasion to nearby parts of the body. Cancers may also spread to more distant parts of the body through the lymphatic system or bloodstream. Cancers may be a result of gene damage due to tobacco use, certain infections, radiation, lack of physical activity, obesity, and/or environmental pollutants. Cancers may also be a result of existing genetic faults within cells to cause diseases due to genetic heredity. Screenings may be used to detect cancers before any noticeable symptoms appear and treatment may be given to those who are at higher risks of developing cancers (e.g., people with a family history of cancers). Examples of screening techniques for cancer include but are not limited to physical examination, blood or urine tests, medical imaging, and/or genetic testing. Non-limiting examples of cancers include: bladder cancer, breast cancer, colon and rectal cancer, endometrial cancer, kidney or renal cell cancer, leukemia, lung cancer, melanoma, Non-Hodgkin lymphoma, pancreatic cancer, prostate cancer, ovarian cancer, stomach cancer, wasting disease, and thyroid cancer.

Fibrotic Diseases

Fibrotic disease represents one of the largest groups of disorders for which there is no effective therapy. Fibrotic diseases are characterized by excessive scarring due to excessive production, deposition, and contraction of extracellular matrix. This process usually occurs over many months and years, and can lead to organ dysfunction or death. Examples of fibrotic diseases include, but are not limited to, idiopathic pulmonary fibrosis, organ fibrosis, interstitial lung disease, skin fibrosis, diabetic nephropathy, liver fibrosis, liver cirrhosis, nonalcoholic steatohepatitis (NASH), rheumatoid arthritis, fibrosarcomas, keloids and hypertrophic scars, arteriosclerosis, kidney disease, macular degeneration, retinal and vitreal retinopathy, surgical complications, chemotherapeutic drug-induced fibrosis, radiation-induced fibrosis, accidental injury, burns, local scleroderma, and systemic scleroderma. Rheumatoid arthritis and other connective tissue disorders often have associated lung pathologies. Lung fibrosis alone can be a major cause of death in scleroderma lung disease, idiopathic pulmonary fibrosis, radiation- and chemotherapy-induced lung fibrosis and in conditions caused by occupational inhalation of dust particles.

Tissue fibrosis is generally considered to arise due to a failure of the normal wound healing response to terminate. After injury, new connective tissue needs to be synthesized. During this process, mesenchymal fibroblasts become "activated" in that they proliferate and migrate into the wound and synthesize elevated levels of matrix proteins, including collagen and fibronectin. The mesenchymal cells activated during tissue repair and wound healing in kidney and liver are called mesangial cells and stellate cells, respectively. The fibroblasts present in a wound are a specialized form of fibroblasts termed myofibroblasts as they express elevated levels of α-SMA and consequently display a markedly enhanced ability to contract extracellular matrix. This aspect of fibroblast function is necessary for wound closure. Myofibroblasts are present in abundance within fibrotic lesions and thus contribute to the excessive scarring observed in lesions of fibrotic disease. Myofibroblasts in fibrotic tissues are derived from at least three sources: expansion and activation of resident tissue fibroblasts, transition of epithelial cells into mesenchymal cells (epithelial-mesenchymal transition, EMT), and tissue migration of bone marrow-derived circulating fibrocytes. Endothelial to mesenchymal transition (EndoMT) is another possible source of tissue myofibroblasts. EndoMT is a biological process in which endothelial cells lose their specific markers and acquire a mesenchymal or myofibroblastic phenotype and express mesenchymal cell products such as α-SMA and type I collagen. Similar to EMT, EndoMT can be induced by TGFβ.

Reduced endoglin expression is shown to attenuate increased collagen expression in lungs and kidneys subjected to increased venous pressure and decreased perfusion and to limit fibrosis in the RV and/or LV in models of heart failure and pulmonary hypertension. Thus, it is envisioned that the compositions of the invention can be used to treat fibrotic diseases (e.g., organ fibrosis) where endoglin plays a role in modulating fibrotic signaling.

Administration and Dosage

The methods described herein feature administration of a composition that inhibits endoglin activity. The composition can be formulated for use in a variety of drug delivery systems. One or more physiologically acceptable excipients or carriers can also be included in the composition for proper formulation. Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The pharmaceutical composition can be used for parenteral, intranasal, topical, oral, or local administration, such as by a transdermal means, for prophylactic and/or therapeutic treatment. The pharmaceutical composition can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that include the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques or may be sterile filtered. The resulting aqueous solutions may be packaged for use as is or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a subject diagnosed as being at risk for heart failure (e.g., having lower levels of soluble endoglin, as described in U.S. patent application Ser. No. 13/288,493). Compositions of the invention can be administered to the subject (e.g., a human) in an amount sufficient to delay, reduce, or preferably prevent the onset of the disorder. In therapeutic applications, compositions are administered to a subject (e.g., a human) already suffering from heart failure of any of the disorders described herein in an amount sufficient to cure or at least partially arrest the symptoms of the disorder and its complications. An amount adequate to accomplish this purpose is defined as a "therapeutically effective amount," an amount of a compound sufficient to substantially improve at least one symptom associated with the disease or a medical condition. For example, in the treatment of heart failure, an agent or compound that decreases, delays, suppresses, or arrests any symptom of the condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the subject. The therapeutically effective amount of the compositions of the invention and used in the methods of this invention applied to mammals (e.g., humans) can be determined by the treating physician with consideration of individual differences in age, weight, and the condition of the mammal. The agents of the invention are administered to a subject (e.g. a mammal, such as a human) in an effective amount, which is an amount that produces a desirable result in a treated subject (e.g., reduction of cardiac fibrosis). Therapeutically effective amounts can also be determined empirically by those of skill in the art.

Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The compounds of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

Combination Therapy
Anticancer/Anti-Proliferative Drugs

The composition of the invention can be formulated or administered in combination with one or more anticancer drugs to improve clinical efficacy by reducing cardiotoxicity and cardiac damage side effects of prolonged use of anticancer drugs. Examples of anticancer agents include, but are not limited to: chemotherapeutic agents (e.g., arsenic trioxide, cisplatin, carboplatin, chlorambucil, melphalan, nedaplatin, oxaliplatin, triplatin tetranitrate, satraplatin, imatinib, nilotinib, dasatinib, and radicicol, an alkylating agent, an anthracycline, an epothilone, a histone deacetylase inhibitor, an inhibitor of topoisomerase I, an inhibitor of topoisomerase II, a cytoskeletal disruptor, a kinase inhibitor, a monoclonal antibody, a peptide antibiotic, a nucleotide analog/precursor analog, a retinoid, and a vinca alkaloid), immunomodulatory agents (e.g., methotrexate, leflunomide, cyclophosphamide, cyclosporine A, minocycline, azathioprine, antibiotics (e.g., tacrolimus), methylprednisolone, corticosteroids, steroids, mycophenolate mofetil, rapamycin, mizoribine, deoxyspergualin, brequinar, T cell receptor modulators, and cytokine receptor modulators), antiangiogenic agents (e.g., bevacizumab, suramin, and etrathiomolybdate), mitotic inhibitors (e.g., paclitaxel, vinorelbine, docetaxel, abazitaxel, ixabepilone, larotaxel, ortataxel, tesetaxel, vinblastine, vincristine, vinflunine, and vindesine), nucleoside analogs (e.g., gemcitabine, azacitidine, capecitabine, carmofur, cladribine, clofarabine, cytarabine, decitabine, floxuridine, fludarabine, fluorouracil, mercaptopurine, pentostatin, tegafur, and thioguanine), DNA intercalating agents (e.g., doxorubicin, actinomycin, bleomycin, mitomycin, and plicamycin), topoisomerase inhibitors (e.g., irinotecan, aclarubicin, amrubicin, belotecan, camptothecin, daunorubicin, epirubicin, etoposide, idarubicin, mitoxantrone, pirarubicin, pixantrone, rubitecan, teniposide, topotecan, valrubicin, and zorubicin), folate antimetabolites (e.g., pemetrexed, aminopterin, methotrexate, pralatrexate, and raltitrexed), mitocans (e.g., sodium dichloroacetate and 3-bromopyruvic acid), and other targeting agents (e.g., agents that target particular enzymes or proteins involved in cancer or agents that target particular organs or types of cancers), and combinations thereof.

Immunosuppressive Agents

The compositions of the invention can be used in combination with an immunosuppressive agent or a drug that inhibits or prevents activity of the immune system. These agents are used to prevent rejection of transplanted organs and tissues, treat autoimmune diseases, and treat some non-autoimmune inflammatory disease. Examples of immunosuppressive agents include, but are not limited to, glucocorticoids (e.g., hydrocortisone, cortisone, prednisone, prednisolone, methylprednisolone, dexamethasone, betamethasone, triamcinolone, beclometasone, fludrocortisones, deoxycorticosterone, and aldosterone), cytostatics (e.g., nitrogen mustards, nitrosoureas, platinum compounds, cyclophosphamide, methotrexate, azathioprine, mercaptopurine, pyrimidine, fluorouracil, and protein synthesis inhibitors, dactinomycin, anthracyclines, mitomycin C, bleomycin, mithramycin), antibodies (e.g., T-cell receptor directed antibodies (e.g, muromonab-CD3), IL-2 receptor directed antibodies (e.g., basiliximab, and daclizumab), drugs acting on immunophilins (e.g., ciclosporin, tacrolimus, and sirolimus), interferons, opiods, and TNF binding proteins.

Prevention Drugs for Cardiovascular Diseases

Compositions of the invention can be administered in combination with one or more drugs that are used as secondary prevention drugs for cardiovascular diseases. Examples of preventative drugs include, but are not limited to, β blockers (e.g., nonselective agents, e.g., alprenolol, carteolol, oxprenolol, sotalol, timolol, e.g., $β_1$-selective agents, e.g., acebutolol, betaxolol, celiprolol, metoprolol, e.g., $β_2$-selective agents, e.g., butaxamine, e.g., $β_3$-selective agents, e.g., SR 59230A), statins (e.g., atorvastatin, cerivastatin, fluvastatin, lovastatin, mevastatin, pravastatin, simvastatin, and rosuvastatin), fibrates (e.g., bezafibrate, ciprofibrate, clofibrate, gemfibrozil, and fenofibrate), biguanides (e.g., metformin, phenformin, buformin, and proguanil), antihypertension agents, and/or ACE inhibitors (e.g., sulfhydryl-containing agents, e.g., captopril, zofenopril, e.g., dicarboxylate-containing agents, e.g., enalapril, ramipril, quinapril, perindopril, imidapril, e.g., phosphate-containing agents, e.g., fosinopril).

Anti-Neurodegenerative Drugs

The composition of the invention can be administered in combination with one or more anti-neurodegenerative drugs. Examples of anti-neurodegenerative drugs include, but are not limited to, acetylcholinesterase inhibitors (e.g., donepezil, galantamine, and rivastigmine), anti-glutamate agent (e.g., amantadine, GABA-ergic, valproic acid), reserpine, tetrabenazine, typical/atypical neuroleptics, tricyclic antidepressants, SSRIs, carbamazepine, baclofen, tizanidine, hydergine, choline, piracetam, and lamotrigine.

Antifibrotic Agents

The compositions of the invention can also be administered in combination with one or more antifibrotic agents. Examples of antifibrotic agents include, but are not limited to pentoxyphiline, tocopherol, vitamin E, pioglitazone, INT 747, peginterferon 2b, infliximab, ribavirin, glycyrrhizin, candesartan, losartan, irbesartan, ambrisentan, FG-3019, warfarin, insulin, colchicines, peginterferon 2a, etanercept, pirfenidone, nintedanib, and IL-10. Typically, an agent can be identified as an antifibrotic agent if it possesses one or more of the following characteristics: 1.) eliminate the cause(s) of injury and their mediators; 2.) reduce inflammation and the immune response; 3.) target specific signaling: receptor-ligand interaction, intracellular signaling (e.g., the renin-angiotensin system, PPARγ, farnesoid, FXR, PXR, or LXR signaling, or NF-κB signaling); 4.) reduce fibrogenesis and/or inhibit matrix synthesis; and 5.) resolve fibrosis by increasing scar matrix degradation, stimulating apoptosis of stellate cells, or cell transplantation.

The following examples are intended to illustrate, rather than limit, the invention.

EXAMPLES

Example 1: Experimental Methods

Reagents

Polyclonal Abs against human calcineurin, α-SMA, phosphorylated (p)Smad3, and total Smad2/3 were purchased from Cell Signaling Technology (2614S; Danvers, Mass.), Sigma-Aldrich (A2547; St. Louis, Mo.), and Cell Signaling Technology (8769S and 3102S), respectively. Goat polyclonal antibodies against mouse endoglin, Type I collagen, and α-SMA were purchased from R&D Systems (BAF1320), Santa Cruz (SC-25974), and Sigma-Aldrich (A2547), respectively. Rabbit polyclonal antibodies to mouse calcineurin (2614S) were purchased from Cell Signaling. Polyclonal antibodies to mouse pSmad-3 (9520), and pERK-1/2 (SC-134900) were purchased from Cell Signaling and Santa-Cruz. Polyclonal antibodies to mouse total Smad-3 (SC-101154) and total ERK (SC-135900) were purchased from Santa-Cruz. Sugen (SU5416) was purchased from Sigma-Aldrich. An IgG1 antibody that binds human and mouse endoglin (TRC105) was kindly provided by Tracon Pharmaceuticals, San Diego, Calif. An enzyme linked immunosorbent assay (ELISA) kit for the detection of active TGFβ1 levels in mice was purchased from R&D Systems.

Mouse Model of Pharmacologically Induced Right Ventricular Pressure Overload

Animals were treated in compliance with the Guide for the Care and Use of Laboratory Animals (National Academy of Science), and protocols were approved by the Tufts Medical Center Institutional Animal Care and Use Committee (Boston, Mass.). Adult, male, 12- to 14-week-old C57BL/6 WT and congenic Eng+/− mice received once-weekly intraperitoneal injections of Sugen and were exposed to either normoxic conditions (room air) or chronic normobaric hypoxia (10% $O_2$), as previously described in Ciuclan et al., *Am J Respir Crit Care Med.* 184:1171-1182, 2011. After 5 weeks of exposure to either Sugen+ Normoxia (Su-Norm) or Sugen+ Hypoxia (Su-Hypox), mice underwent hemodynamic analysis with a RV conductance catheter (Millar Instruments Inc., Houston, Tex.), as described below, and tissue was then obtained for further analysis.

Mouse Model of Surgically Induced Right Ventricular Pressure Overload

Animals were treated in compliance with the Guide for the Care and Use of Laboratory Animals (National Academy of Science), and protocols were approved by the Tufts Medical Center Institutional Animal Care and Use Committee. Adult, male, 12-14 week old C57BL/6 WT and congenic Eng+/− mice underwent pulmonary artery constriction (PAC) as previously described in Urashima et al., *Heart Circ Physiol.* 2008:295:H1351-H1368, 2008 and Kapur et al., *PLoS ONE.* 8:e70802, 2013. Specifically, mice were intubated using a 24G angiocath and mechanically ventilated (Harvard Apparatus) at 95 breaths per minute with a tidal volume of 0.3 mL with 2.0-2.5% Isoflurane and 100% flow-through oxygen. Depth of anesthesia was monitored by assessing palpebral reflex, toe pinch, respirations, and general response to touch. Using sterile technique, a left thoracotomy was performed to isolate and encircle the main pulmonary artery using a 7-0 nylon suture that is then tied tightly around a pre-sterilized, blunt end needle. After de-airing, the thorax is closed with layered 6-0 Dexon sutures to eliminate the risk of pneumothorax. Post-operative analgesia is immediately provided with subcutaneous buprenorphine 0.1 mL, which is continued twice daily and as needed for an additional 72 hours. Severe RVPO was induced by PAC with a 25G needle for 7 days in WT and Eng+/− mice. To investigate the role of endoglin in RVPO, WT mice received 15 mg/kg of either a neutralizing antibody to endoglin (N-Eng Ab; TRC105; Tracon Pharma) or an IgG1 control antibody (IgG Ab; R&D Systems) via single intraperitoneal injection 1 day prior to and 3 days after induction of severe RVPO. To study the effect of blocking endoglin activity after induction of RVPO, WT mice were randomized to receive biweekly IP injections for three weeks of 15 mg/kg N-Eng Ab or IgG control Ab beginning three weeks after induction of moderate RVPO using a 23G needle for PAC. The antibody dose was based on a previous clinical study demonstrating effective saturation of endoglin receptors described in Rosen et al., *Clin Cancer Res.* 18:4820-4829, 2012. After 7 days of severe PAC or 3 to 6 weeks of moderate RVPO, mice underwent hemodynamic analysis with a RV conductance catheter (Millar Inc) as previously described in Kapur et al., *PLoS ONE.* 8:e70802, 2013.

Briefly, mice were anesthetized with 2.0% isoflurane administered via a non-invasive nose-cone. Body temperature was monitored by a rectal thermistor probe and maintained at 37.5° C. with heating pads and a cycling heat lamp. In the supine position, the right external jugular vein was surgically isolated. A conductance catheter was advanced into the right ventricle for pressure-volume loop acquisition as described in Kapur et al., *PLoS ONE.* 8:e70802, 2013. After completion of the hemodynamic study, with the animal still under isoflurane anesthesia, the chest was rapidly opened, and the mouse was euthanized by arresting the heart in diastole with 0.3 mL of 1N KCL injected directly into the left ventricle. The heart was then removed and processed for either biochemical or histologic analyses.

Nuclear Factor of Activated T-Cell Activity In Vivo

Nuclear factor of activated T-cell (NFAT)-luciferase (NFAT-Luc) mice with nine copies of an NFAT-binding site from the interleukin (IL)-4 promoter (5'-TGGAAAATT-3') inserted upstream of the luciferase reporter gene, driven by the α-myosin heavy-chain promoter were purchased from The Jackson Laboratory (Bar Harbor, Me.). Eng+/−-NFAT luciferase reporter mice were generated by crossing Eng+/− mice with the NFAT-luciferase mice. Severe RVPO was induced by PAC in 10- to 12-week-old Eng+/+-NFAT-Luc and Eng+/−-NFAT-Luc. After 7 days of severe PAC, RV tissue was then obtained for quantification of luciferase activity using firefly luciferase assays that were carried out as follows: 20 µL of whole RV tissue lysate was added to 100 µL of firefly luciferase assay buffer (Promega, Madison, Wis.). Samples were placed in a luminometer (Luminoskan Ascent; Labsystems Oy, Helsinki, Finland), and luminescence was determined in triplicate per sample over a 10-second interval.

Hemodynamic Assessment of RV Function

All animals underwent terminal hemodynamic evaluation. Right heart catheterization was performed at the time of sacrifice in all animals. Mice were anesthetized with 2.0% isoflurane administered by a noninvasive nose cone. Body temperature was monitored by a rectal thermistor probe and maintained at 37.5° C. with heating pads and a cycling heat lamp. In the supine position, the right common carotid and right external jugular vein were surgically isolated. Silk ties were placed at the distal ends of both vessels while overhand loops were placed at the proximal ends with 7-0 nylon. A Millar PVR-1035 (Millar Instruments) mouse conductance catheter was used for RV recordings. Before insertion, conductance catheter calibration was performed using the cuvette method with freshly heparinized warm blood, then zeroed in warm saline as previously described in Rockman et al., *Proc Natl Acad Sci USA.* 91:2694-2698, 1994 and Kass et al., *Circulation.* 73:596-595, 1986. A transverse venotomy was performed using iris scissors at the proximal end of the external jugular vein. The PVR-1035 catheter was advanced through the superior vena cava and right atrium into the RV, leaving the chest wall intact. Once hemodynamic stability was achieved, steady-state baseline conditions were recorded from the RV. Stroke volume was calculated as end-diastolic minus end-systolic volume. Arterial elastance was calculated under steady-state conditions as end-systolic pressure/stroke volume. Tau, a measure of instantaneous isovolumic relaxation, was calculated using the Glantz method as $P(t)=P_0 e^{-t/\tau_E}+P\alpha$, where P is pressure at time t, $P_0$ is the amplitude constant, $\tau_E$ is the Glantz relaxation constant, and Pα is the nonzero asymptote resulting from pleural and pericardial pressure. RV compliance was calculated as stroke volume divided by peak RV pressure. Pressure-volume loop acquisition and analysis was performed using IOX software (emka TECHNOLOGIES, Paris, France). After completion of the hemodynamic study, with the animal still under isoflurane anesthesia, the chest was rapidly opened, and the mouse was euthanized by arresting the heart in diastole with 0.3 mL of 1 N of KCL injected directly into the LV. The heart was then removed and processed for either biochemical or histologic analyses.

Histologic Quantification of Cardiac Hypertrophy and Fibrosis

RV collagen abundance was quantified by picrosirius red staining as described in Georgescu et al., *Am J Physiol Cell Physiol.* 301:C1046-1056, 2011. Cardiomyocyte cross-sectional area was quantified as described in Patten et al. *J Card Fail.* 14:245-253, 2008.

Loss of Function Studies in Cardiac Fibroblasts

Briefly, adult WT and Eng+/− mice were intubated using a 24G angiocath and mechanically ventilated (Harvard Apparatus) at 95 breaths per minute with a tidal volume of 0.3 mL with 2.0-2.5% Isoflurane and 100% flow-through oxygen. Depth of anesthesia was monitored by assessing palpebral reflex, toe pinch, respirations, and general response to touch. With the animal still under isoflurane anesthesia, the chest was rapidly opened, and the mouse was euthanized by arresting the heart in diastole with 0.3 mL of 1N KCL injected directly into the left ventricle. The heart was then removed and processed for isolation of cardiac fibroblasts, primary culture, and TGFβ1 stimulation as previously described in Kapur et al., *Circulation.* 115:67-75, 2007 and Neuss et al., *Cell Tissue Res.* 286:145-153, 1996. For neutralizing antibody studies in vitro, mouse cardiac fibroblasts were pretreated with 10, 50, or 100 ug/mL of either a N-Eng Ab or control IgG Ab for 24 hours in fibroblast basal medium without supplementation prior to stimulation with TGFβ1 (10 ng/mL). After 24 hours, cells were harvested for analysis. The antibody dose was based on previous studies demonstrating effective neutralization of endoglin activity in endothelium described in Nolan-Stevaux et al., *PLoS ONE.* 7:e5-920, 2012.

Human RV (RVFB) and LV (LVFB) fibroblasts were isolated from myocardial tissue harvested during cardiac surgery at Tufts Medical Center, and mouse RVFB and LVFB were isolated from WT and Eng+/mice. Fibroblasts were stimulated with TGFβ1 for analysis, as previously described in Kapur et al., *Circulation* 125:2728-2738, 2012; Kapur et al., *Circulation.* 115:67-75, 2007; and Neuss et al., *Cell Tissue Res.* 286:145-153, 1996. For calcineurin inhibition studies, human RVFB were pretreated with 5 nM of cyclosporine A (CsA) or vehicle control for 24 hours in fibroblast basal medium (FBM) without supplementation, followed by stimulation with TGFβ1 (10 ng/mL) for 24 hours. For TRPC-6 silencing experiments, 50 μmol/L of siRNA stock was diluted to 5 nmol/L in Optimem (Invitrogen, Carlsbad, Calif.) and combined with 2 μL of Lipofectamine (Invitrogen) diluted in 98 IL of Optimem. After 20 minutes of incubation, cells were exposed to human TRPC-6 siRNA (Catalog No.: 439420; Ambion, Austin, Tex.) or scrambled siRNA (negative control; Catalog No.: 4390844; Ambion). After 48 hours after transfection, cells were treated with TGFβ1 (10 ng/mL) for 16 to 24 hours, then harvested for analysis. For neutralizing Ab studies in vitro, human RVFB and LVFB were pretreated with 10, 50, or 100 μg/mL of either an N-Eng Ab or control IgG Ab for 24 hours in FBM before stimulation with TGFβ1 (10 ng/mL). After 24 hours, cells were harvested for analysis. The Ab dose was based on previous studies demonstrating effective neutralization of endoglin activity in endothelium. All RVFB and LVFB stimulation studies were conducted in triplicate with cells cultured to within three lineage passes only.

Real-Time Quantitative Polymerase Chain Reaction (RT-PCR)

For all cell-based RT-PCR experiments, total RNA was extracted directly using Trizol (Invitrogen), converted to cDNA using a High Capacity cDNA Reverse Transcription Kit (Applied Biosystems). For all RT-PCR experiments, samples were quantified in triplicate using 40 cycles performed at 94° C. for 30 sec., 60° C. for 45 sec, 72° C. for 45 sec using an ABI Prism® 7900 Sequence Detection System with appropriate primers (Table 1) as described in Patten et al. *J Card Fail.* 14:245-253, 2008 and Kapur et al., *Circulation* 115:67-75, 2007.

TABLE 1

Primer Sequences

| | Mouse Primers | |
|---|---|---|
| | Type I collagen | |
| Forward | AAG GGT CCC TCT GGA GAA CC | (SEQ ID NO: 3) |
| Reverse | TCT AGA GCC AGG GAG ACC CA | (SEQ ID NO: 4) |
| | Calcineurin (CN-PP) | |
| Forward | CCACAGGGATGTTGCCTAGTG | (SEQ ID NO: 5) |
| Reverse | GTCCCGTGGTTCTCAGTGGTA | (SEQ ID NO: 6) |
| | Endoglin | |
| Forward | CTG CCA ATG CTG TGC GTG AA | (SEQ ID NO: 7) |
| Reverse | GCT GGA GTC GTA GGC CAA GT | (SEQ ID NO: 8) |
| | α-SMA | |
| Forward | GCATCCACGAAACCACCTA | (SEQ ID NO: 9) |
| Reverse | CACGAGTAACAAATCAAAGC | (SEQ ID NO: 10) |
| | MYH7 | |
| Forward | ATG TGC CGG ACC TTG GAA | (SEQ ID NO: 11) |
| Reverse | CCT CGG GTT AGC TGA GAG ATC A | (SEQ ID NO: 12) |
| | TRPC-6 | |
| Forward | GGC GGC TCT CTA AAG GCT G | (SEQ ID NO: 13) |
| Reverse | TGG GGT AGT AGC CAT ACG GTG | (SEQ ID NO: 14) |
| | Human Primers | |
| | Type I collagen | |
| Forward | GTC GAG GGC CAA GAC GAA G | (SEQ ID NO: 15) |
| Reverse | CAG ATC ACG TCA TCG CAC AAC | (SEQ ID NO: 16) |

TABLE 1-continued

Primer Sequences

Calcineurin (CN-PP)

| | |
|---|---|
| Forward | TGCATCAATTCTTCGACAGG (SEQ ID NO: 17) |
| Reverse | AAGGCCCACAAATACAGCAC (SEQ ID NO: 18) |

α-SMA

| | |
|---|---|
| Forward | CCGACCGAATGCAGAAGGA (SEQ ID NO: 19) |
| Reverse | ACAGAGTATTTGCGCTCCGAA (SEQ ID NO: 20) |

TRPC-6

| | |
|---|---|
| Forward | GCCAATGAGCATCTGGAAAT (SEQ ID NO: 21) |
| Reverse | TGGAGTCACATCATGGGAGA (SEQ ID NO: 22) |

Immunoblot Analysis (Western)

Total protein was extracted and quantified from tissue homogenates or cultured cells as described in Patten et al. *J Card Fail*. 14:245-253, 2008 and Kapur et al., *Circulation*. 115:67-75, 2007. Immunoblot analysis was then performed as previously described in Patten et al. *J Card Fail*. 14:245-253, 2008 and Kapur et al., *Circulation* 115:67-75, 2007, using antibodies for mouse targeted proteins.

Statistical Analysis

Results are presented as mean±standard deviation. Inter-group comparisons were made with two-factor ANOVA. Repeated measures ANOVA were used as needed to account for time. All multiple comparisons versus a control group were performed using Dunnett's method. Kaplan-Meier analysis with log-rank testing was employed for survival analysis. All statistical analyses were performed using SigmaStat Version 3.1 (Systat Software, Inc). An alpha level of P<0.05 was considered to indicate a significant effect or between-groups difference.

Figure 1B:
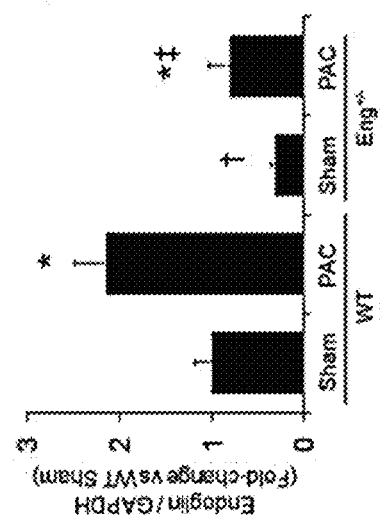
Figure 1C:
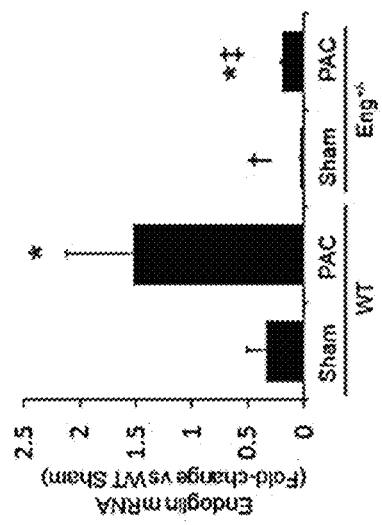
Figure 1F:
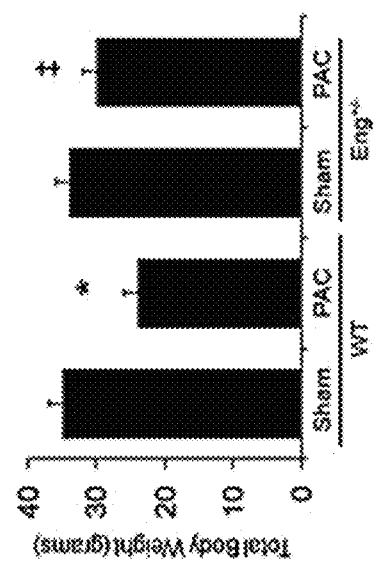
Figure 1E:
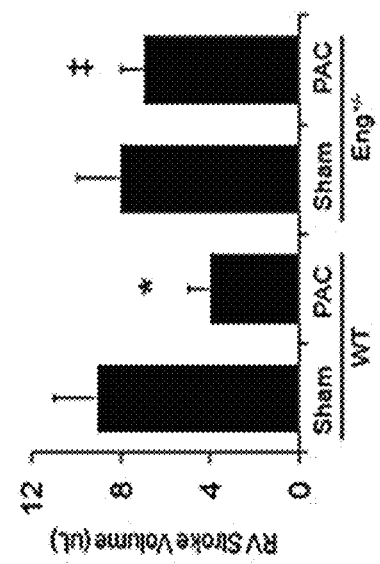
Figure 1D:
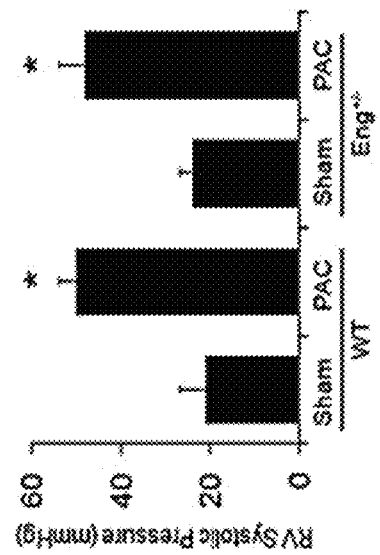

Example 2: Reduced Endoglin Expression Preserves RV Function and Improves Survival in RVPO To explore the functional role of endoglin in RV remodeling Eng+/− mice was studied. Compared to WT, baseline RV endoglin expression was lower in Eng+/− mice (FIGS. 1A-1B). Severe RVPO was then induced by PAC for 7 days in WT and Eng+/− mice. In WT mice, compared to sham controls, PAC increased endoglin levels in the RV, suggesting a direct effect of RVPO on endoglin expression. RVPO also increased endoglin expression in Eng+/− mice, but levels were significantly lower compared to WT mice (FIGS. 1A-1B). The functional impact of reduced endoglin levels in RVPO was then examined. Eng+/− mice demonstrated substantially improved survival (100% versus 58%, respectively, p=0.01) compared with WT mice after PAC (FIG. 1C). Despite equally increased RV systolic pressure in both WT and Eng+/− mice after PAC, RV stroke volume decreased in WT, but not Eng+/− mice (FIG. 1D-1E; Table 2). WT mice also manifest reduced total body weight after RVPO, while Eng+/− mice did not (FIG. 1F). These findings suggest that despite identical degrees of RVPO, reduced endoglin expression in Eng+/− mice preserved RV function and improved survival.

TABLE 2

Characterization of Right Ventricular Pressure Overload in Wild-Type and Eng+/− Mice induced by PAC, Sugen, or Hypoxia

| | Wild Type | | Eng$^{+/-}$ | |
|---|---|---|---|---|
| | Sham (n = 6) | PAC (n = 7) | Sham (n = 6) | PAC (n = 8) |
| Total body weight, g | 35 ± 2 | 24 ± 2* | 34 ± 4 | 28 ± 2 |
| RV weight/tibial length, g/mm | 1.4 ± 0.1 | 3 ± 0.1* | 1.7 ± 0.3 | 2.3 ± 0.1 |
| LV weight/tibial length, g/mm | 6 ± 0.4 | 4 ± 0.3* | 5 ± 0.2 | 4 ± 0.3*,† |
| Hemodynamic variables | | | | |
| RV systolic pressure, mm Hg | 21 ± 6 | 50 ± 4* | 24 ± 3 | 46 ± 9 |
| RV end-diastolic pressure, mm Hg | 4 ± 2 | 8 ± 4 | 2 ± 1 | 4 ± 2 |
| RV +dp/dt, mm Hg/sec | 2358 ± 392 | 3328 ± 1163* | 2064 ± 343 | 3517 ± 1118* |
| RV −dp/dt, mm Hg/sec | 2514 ± 187 | 2613 ± 849 | 2079 ± 341 | 2715 ± 622* |
| RV stroke volume, μL | 9 ± 3 | 4 ± 1* | 8 ± 2 | 7 ± 1† |
| Cardiac output, mL/min | 5 ± 1 | 2 ± 1* | 4 ± 1 | 4 ± 1† |
| Heart rate, beats per min | 540 ± 62 | 532 ± 51 | 509 ± 13 | 521 ± 24 |

| | Wild Type | | Eng$^{+/-}$ | |
|---|---|---|---|---|
| | Su-Norm | Su-Hypox | Su-Norm | Su-Hypox |
| Total body weight, g | 27 ± 2 | 27 ± 1 | 29 ± 2 | 28 ± 2 |
| RV weight/tibial length, g/mm | 1.2 ± 0.4 | 1.4 ± 0.4 | 1.4 ± 0.1 | 1.5 ± 0.1 |
| LV weight/tibial length, g/mm | 4.8 ± 3 | 4.4 ± 3 | 4.9 ± 2 | 5.3 ± 1 |
| Hemodynamic variables | | | | |
| RV systolic pressure, mm Hg | 23 ± 2 | 36 ± 2 | 24 ± 4 | 34 ± 3 |
| RV end-diastolic pressure (mm Hg) | 2 ± 1 | 3 ± 1 | 3 ± 3 | 2 ± 2 |
| RV +dp/dt, mm Hg/sec | 2259 ± 217 | 3203 ± 456* | 2476 ± 257 | 2924 ± 156* |
| RV −dp/dt, mm Hg/sec | 2162 ± 149 | 3212 ± 642 | 2333 ± 418 | 2100 ± 493 |
| RV stroke volume, μL | 7 ± 3 | 8 ± 3 | 8 ± 1 | 8 ± 2 |

TABLE 2-continued

Characterization of Right Ventricular Pressure Overload in Wild-Type
and Eng+/− Mice induced by PAC, Sugen, or Hypoxia

| | | | | |
|---|---|---|---|---|
| Cardiac output, mL/min | 3794 ± 1827 | 3898 ± 1670 | 4150 ± 1345 | 3995 ± 1529 |
| Heart rate, beats per min | 507 ± 37 | 504 ± 28 | 514 ± 52 | 506 ± 53 |

LV indicates left ventricular; RV, right ventricular.
*$P < 0.01$ versus Su-Norm (n = 6/group).

Figure 1G:
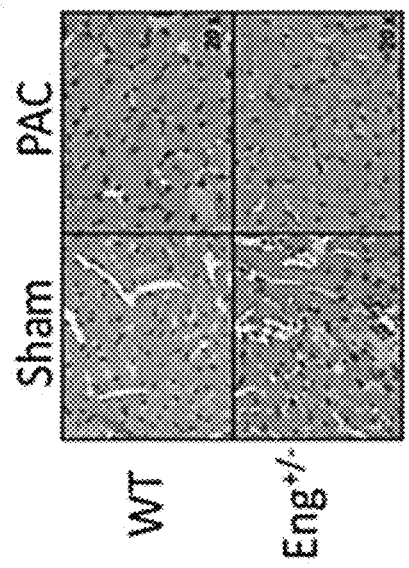
Figure 1H:
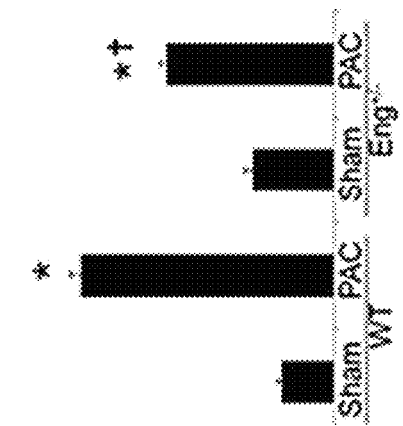

Example 3: Reduced Endoglin Expression Limits RV Fibrosis and TGFβ1/Calcineurin Activity in RV Pressure Overload To study the mechanism underlying improved survival in Eng+/− mice, changes in RV structure were examined. RVPO increased RV mass in WT, not Eng+/− mice (Table 2). RV cardiomyocyte cross-sectional area was increased in both WT and Eng+/− mice after RVPO, but the degree of hypertrophy was lower in Eng+/− mice (FIGS. 1G-1H). RVPO also increased RV fibrosis in WT, but not Eng+/− mice (FIGS. 2A-2B). Consistent with this observation, collagen levels were increased in WT, but not Eng+/− mice after RVPO (FIG. 2C). These findings suggest that endoglin regulates changes in RV structure in RVPO.

Figure 1I:
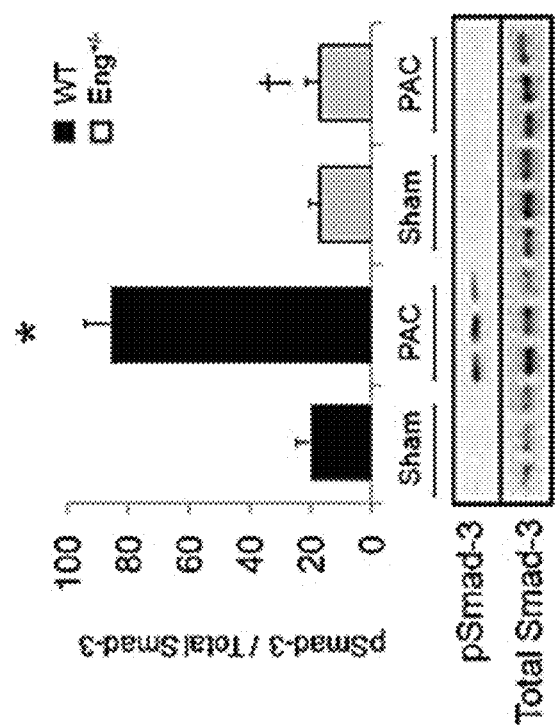
Figure 1J:
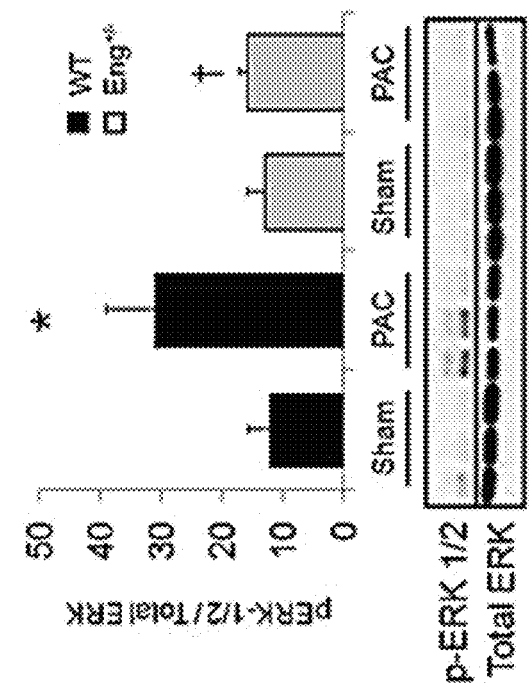
Figures 2G, 2H, 2I:
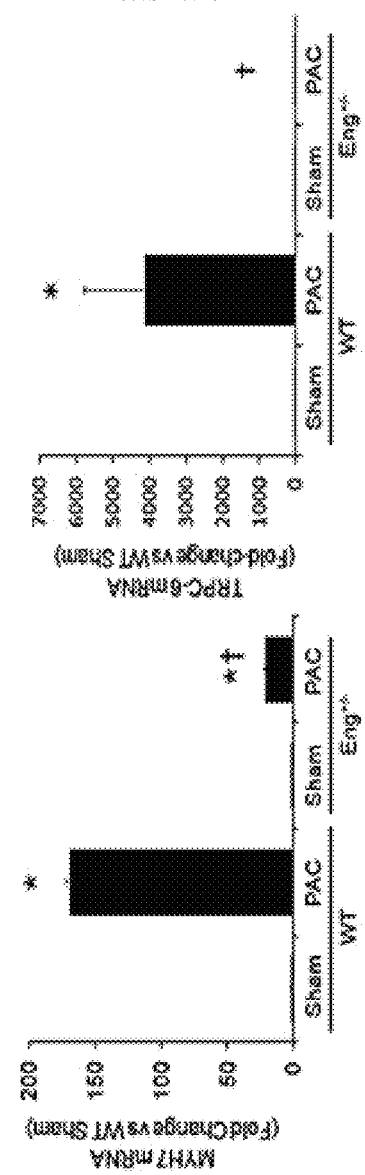

Next, TGFβ1 signaling in RVPO was studied. Despite equally increased active TGFβ1 protein levels in WT and Eng+/− mice (FIG. 2D), levels of pSmad-3 and pERK-1/2 were increased in WT mice, but not Eng+/− mice (FIGS. 1I-1J). Reduced levels of calcineurin mRNA and protein expression in Eng+/− mice was observed compared to WT after RVPO (FIG. 2E-F). Levels of downstream targets of calcineurin activity including MYH7 and TRPC-6 were also reduced in Eng+/− mice compared to WT after RVPO (FIGS. 2G-2H). Levels of α-SMA mRNA were also increased in WT, but not Eng+/− mice after RVPO, indicating reduced fibroblast to myofibroblast conversion in Eng+/− mice (FIG. 2I). These observations suggest that canonical and non-canonical TGFβ1 pathways that promote cardiac fibrosis are activated by RVPO and require endoglin. Furthermore, reduced endoglin levels limited RV expression of both calcineurin and α-SMA, key components of myofibroblast transformation, supporting an important role for endoglin in RV remodeling.

Figure 9:
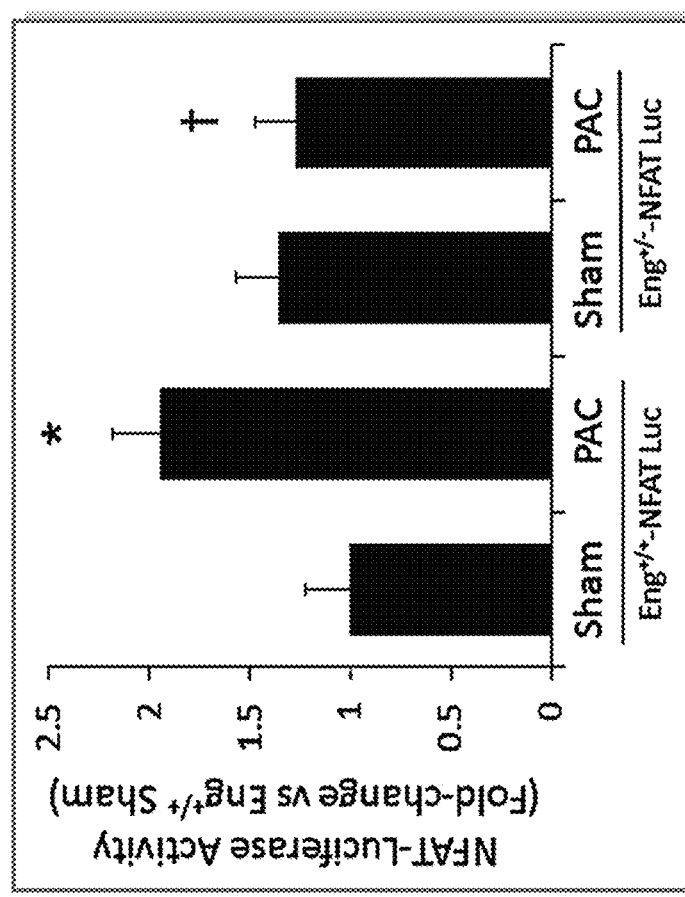
FIG. 9 is a graph showing that reduced endoglin expression limits calcineurin activity in RV pressure overload. Luciferase activity in RV lysates from Eng+/+-NFAT-Luc and Eng+/−-NFAT-Luc mice subjected to 7 days of severe RVPO. *P<0.05 vs. Eng+/+-NFAT-Luc Sham; †P<0.05 vs. Eng+/+-NFAT-Luc PAC. PAC indicates pulmonary artery construction; RVPO, RV pressure overload.

To further explore whether endoglin regulates calcineurin activity, RVPO was induced in Eng+/+-NFAT-Luc and Eng+/−-NFAT-Luc mice. RVPO increased luciferase activity in total RV lysates from Eng+/+-NFAT-Luc, not Eng+/−-NFAT-Luc, mice (FIG. 9). These observations suggest that, in addition to regulating canonical and noncanonical TGFβ1 pathways that promote cardiac fibrosis, reduced endoglin levels in the RV limit calcineurin expression and activity, including myofibroblast transformation. These findings support an important role for endoglin-mediated regulation of TGFβ1 and calcineurin activity in RV remodeling.

Figure 2L:
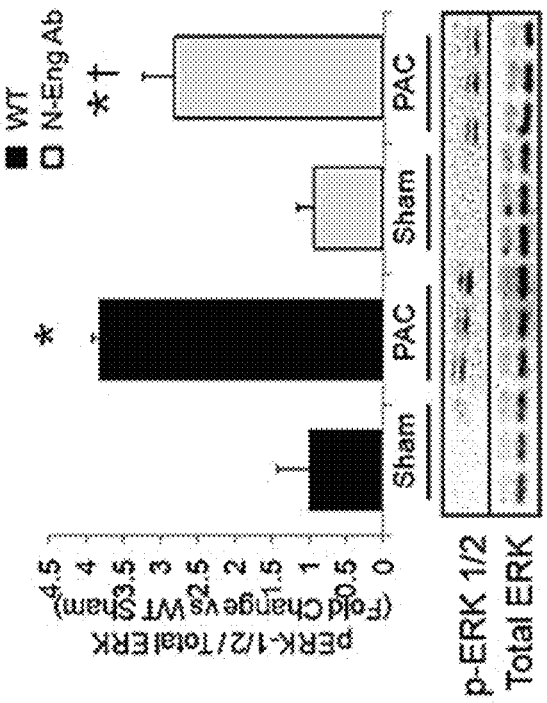
Figure 2M:
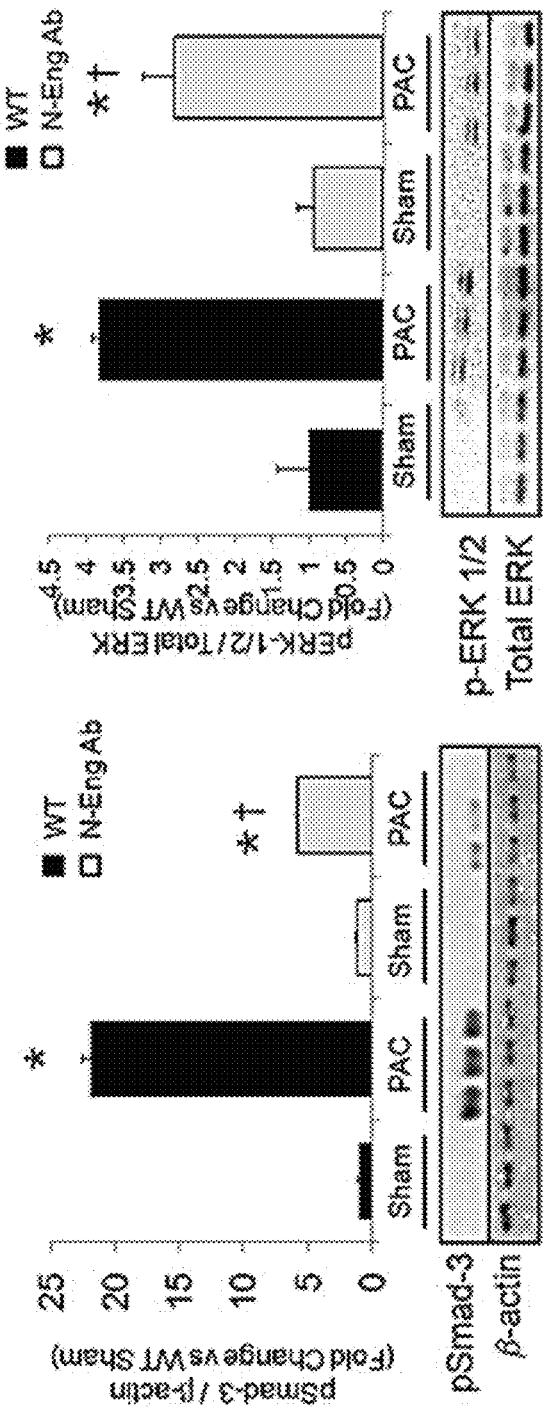
Figure 3D:
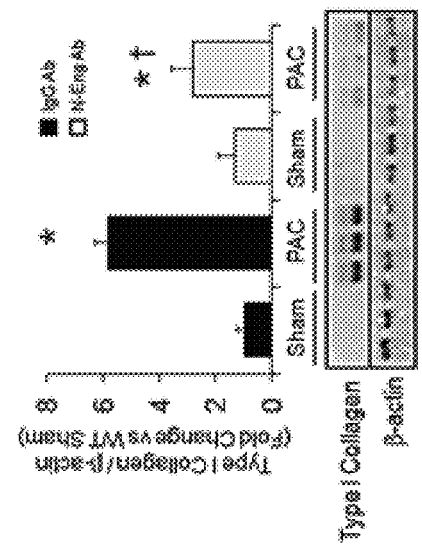
Figure 3E:
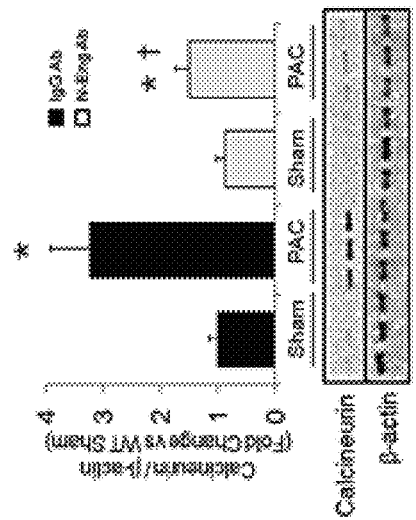
Figure 3F:
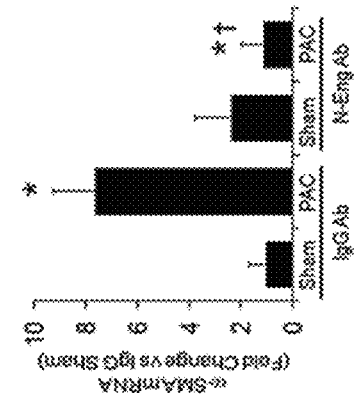
Figure 3G:
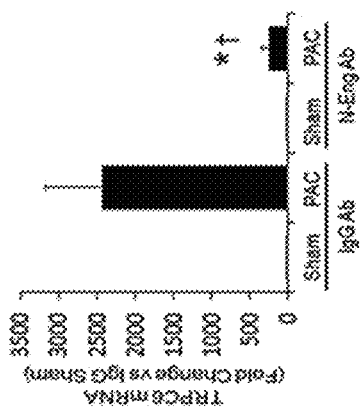
Figure 3H:
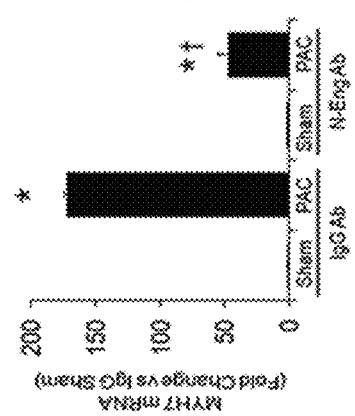

Example 4: Neutralizing Endoglin Activity Prevents RV Fibrosis and Improves Survival in RVPO To confirm whether calcineurin expression requires endoglin in RVPO, WT mice were pretreated with a N-Eng Ab (TRC105) or control IgG Ab before PAC. Despite equally increased RV systolic pressures in both groups (Table 3), N-Eng Ab treatment improved survival after 7 days of severe RVPO compared to IgG treatment (FIG. 3A). RV cardiomyocyte cross sectional area was increased in both groups, but a trend towards lower cardiomyocyte hypertrophy was observed in N-Eng Ab treated mice compared to IgG controls (p=0.09) (FIG. 2J-2K). RV mass was also increased in both groups, but the degree of hypertrophy was attenuated in N-Eng Ab treated mice after RVPO (Table 1). RV fibrosis was significantly reduced in mice receiving the N-Eng Ab (FIG. 3B-3C) along with reduced Type I collagen and calcineurin levels (FIG. 3D-3E) compared to the IgG group after RVPO. Levels of pSmad-3 and pERK-1/2 were also reduced in the N-Eng Ab group, compared to the IgG group after RVPO (FIG. 2L-2M). Levels of downstream targets of calcineurin activity including MYH7, TRPC-6, and α-SMA mRNA were also reduced in the N-Eng Ab group after RVPO (FIGS. 3F-3H).

TABLE 3

Characterization of Right Ventricular Pressure Overload induced by
severe PAC in Wild-Type Mice Pre-treated with a Neutralizing Antibody
Against Endoglin (N-Eng Ab) or IgG-Isotype Control Antibody (IgG)

| | Wild Type | | Wild Type + N-Eng Ab | |
|---|---|---|---|---|
| | Sham | PAC | Sham | PAC |
| Total body weight, g | 29 ± 2 | 23 ± 2* | 28 ± 1 | 24 ± 2* |
| RV weight/tibial length, g/mm | 1.5 ± 0.01 | 2.5 ± 0.01* | 1.5 ± 0.01 | 1.9 ± 0.01*,† |
| LV weight/tibial length, g/mm | 6 ± 0.01 | 4 ± 0.01* | 6 ± 0.01 | 5 ± 0.02* |
| Hemodynamic variables | | | | |
| RV systolic pressure, mm Hg | 22 ± 3 | 48 ± 4* | 24 ± 3 | 53 ± 9* |
| RV end-diastolic pressure, mm Hg | 4 ± 1 | 7 ± 4 | 3 ± 2 | 4 ± 2 |
| RV +dp/dt, mm Hg/sec | 2374 ± 429 | 3189 ± 982 | 2171 ± 283 | 4130 ± 563* |
| RV −dp/dt, mm Hg/sec | 2419 ± 304 | 2810 ± 891 | 1963 ± 257 | 3287 ± 350* |
| RV stroke volume, μL | 8 ± 3 | 4 ± 1* | 8 ± 2 | 5 ± 1* |
| Cardiac output, mL/min | 4.3 ± 1 | 1.8 ± 1* | 4.0 ± 1 | 2.4 ± 0.2 |
| Heart rate, beats per min | 538 ± 25 | 548 ± 33 | 512 ± 59 | 514 ± 52 |

PAC indicates pulmonary artery constriction; LV, left ventricular; RV, right ventricular.
*$P < 0.01$ versus sham;
†$P < 0.01$ versus wild-type PAC (n = 6/group).

Figure 7D:
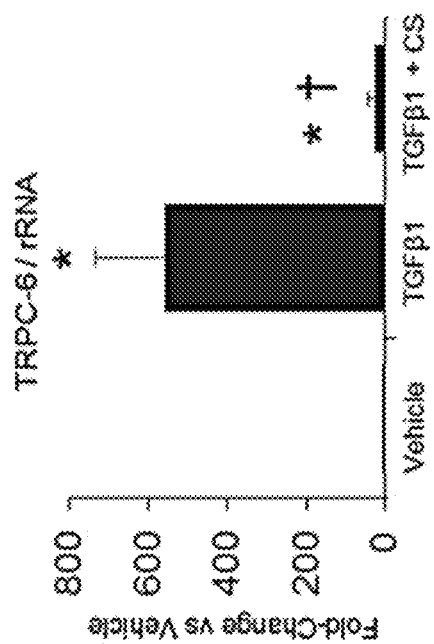
Figure 7E:
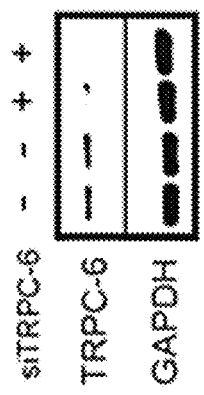
Figure 7F:
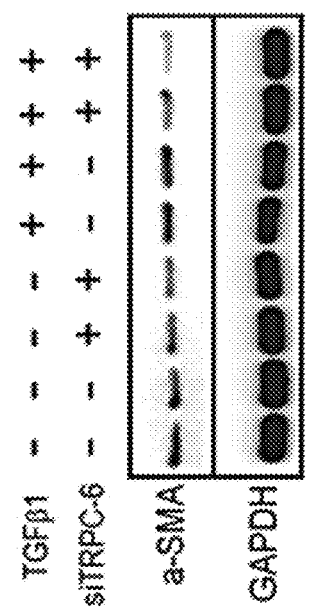

Example 5: Endoglin is Required for Calcineurin Expression and Myofibroblast Conversion in RV Fibroblasts The role of endoglin as a regulator of calcineurin expression in cultured fibroblasts from the RV (RVFB) and LV (LVFB) of WT and Eng+/− mice was studied. Human RVFB were stimulated with TGFβ1 in the presence or absence of the calcineurin inhibitor, CsA. Pretreatment with cyclosporine attenuated TGFβ1-mediated increases in protein and mRNA levels of calcineurin and α-SMA (FIG. 7A through 7C). TGFβ1 stimulation also increased TRPC-6 mRNA expression in human RVFB, which was prevented by cyclosporine treatment (FIG. 7D). To examine the role of TRPC-6 in RV myofibroblast transformation, a siRNA against TRPC-6 was used (siTRPC-6), which achieved a greater than 75% knockdown of TRPC-6 protein expression in RVFB (FIG. 7E). Silencing TRPC-6 attenuated TGFβ1-mediated up-regulation of calcineurin and α-SMA in human RVFB (FIG. 7F). These data indicate that TGFβ1 increases expression of TRPC-6 and α-SMA in a calcineurin-dependent manner in human RV fibroblasts.

Figure 3I:
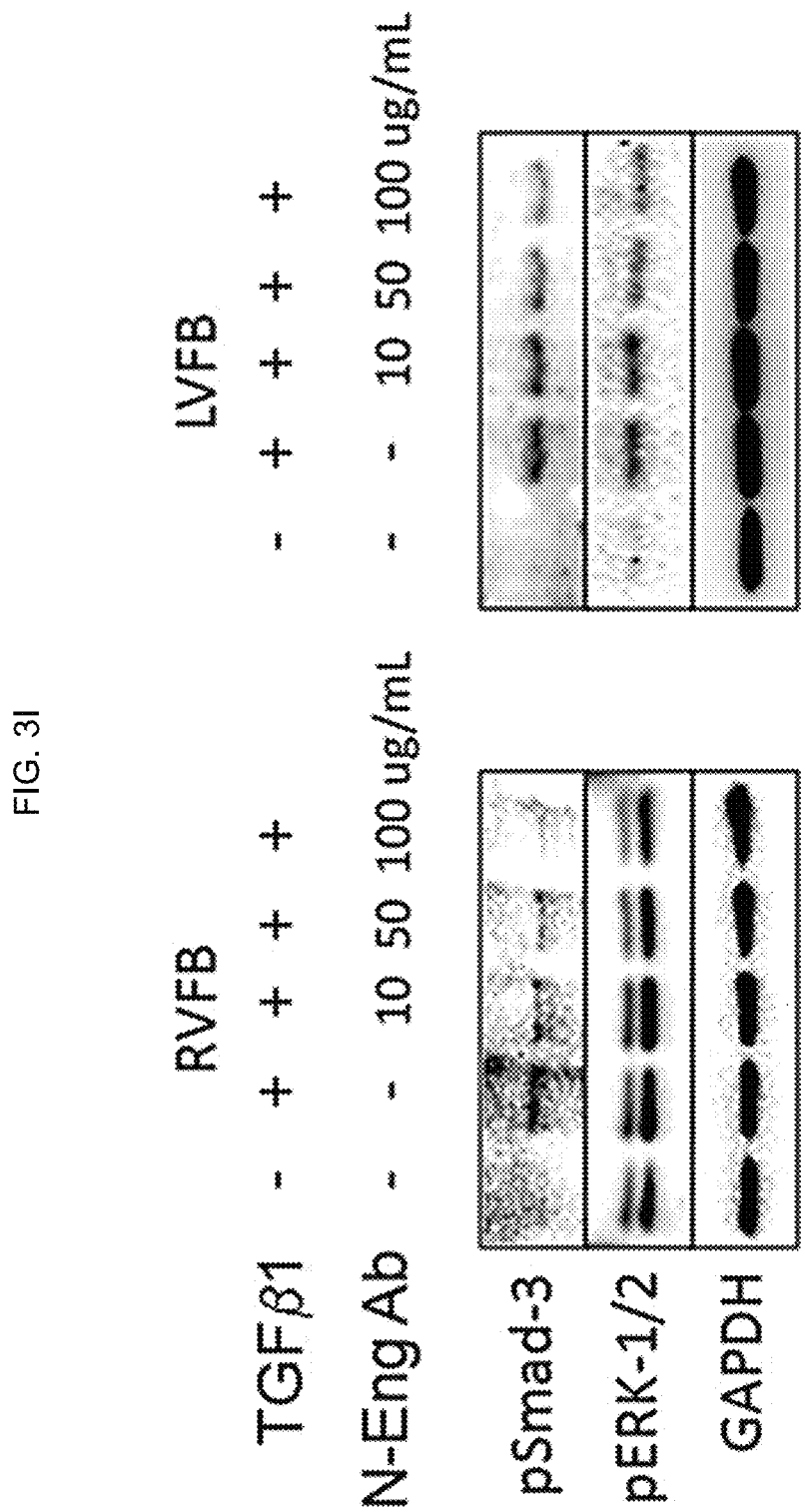
Figure 4A:
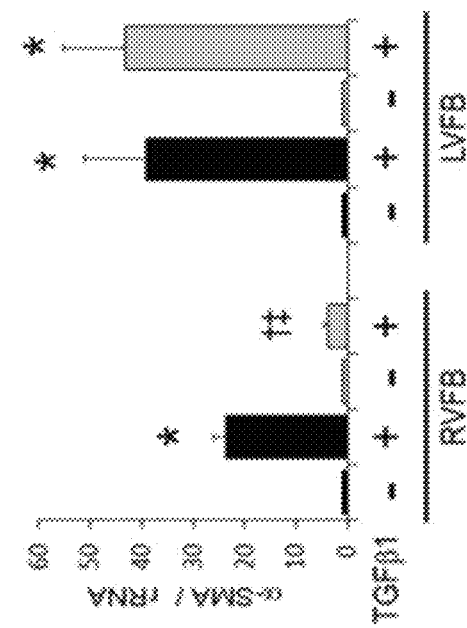
Figure 4B:
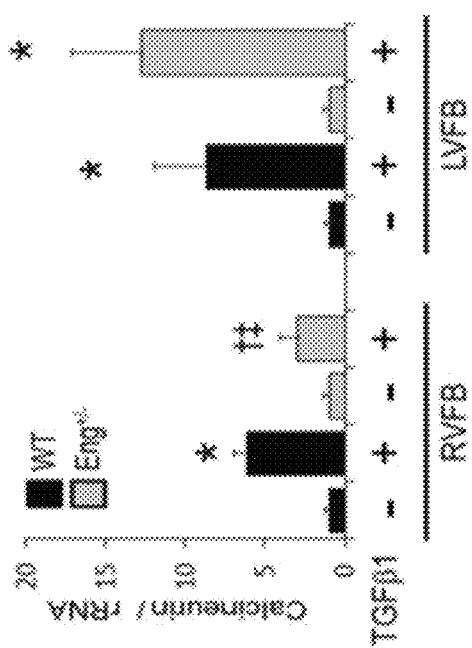
Figure 4C:
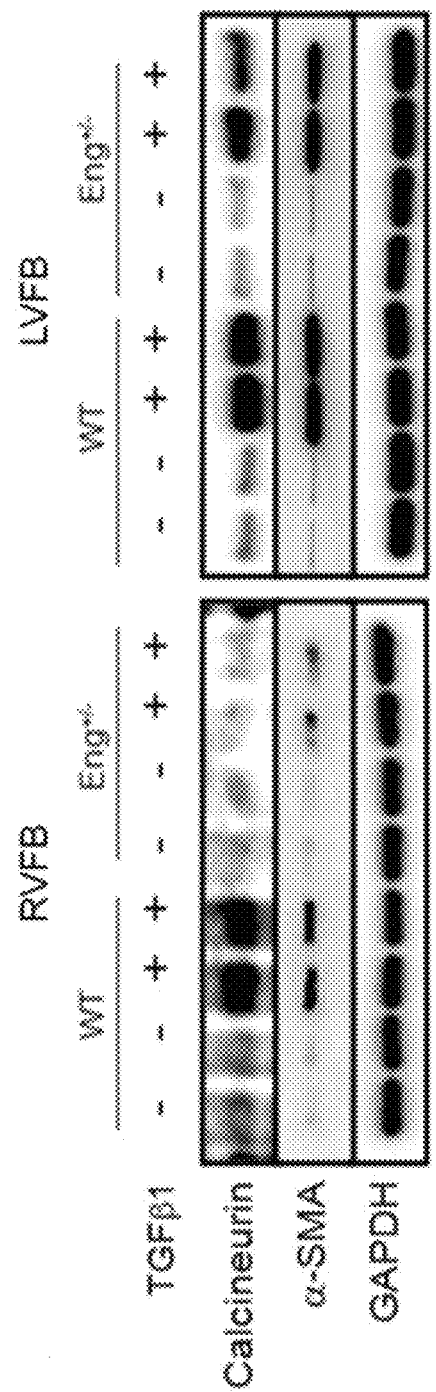
Figure 4D:
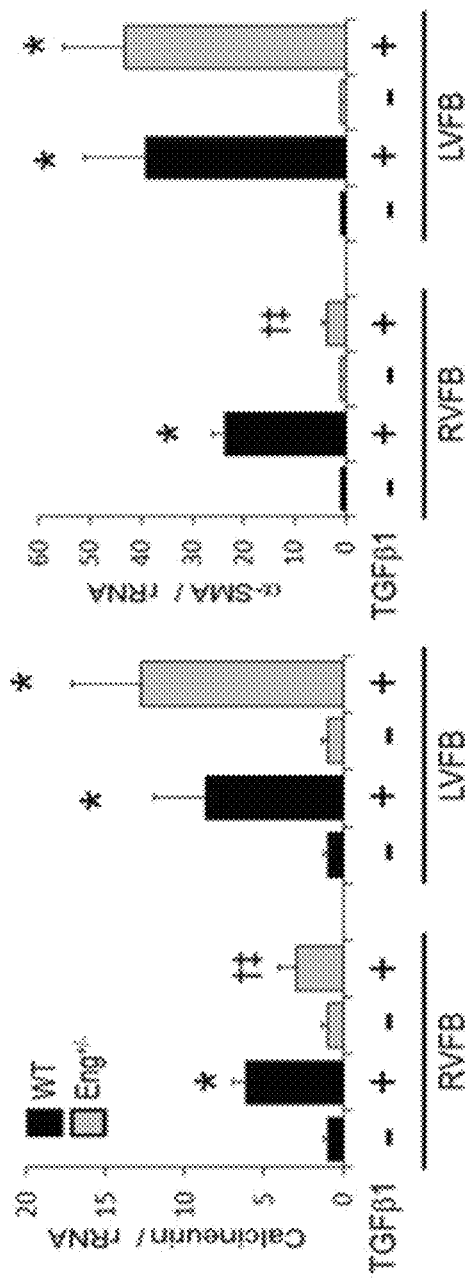

In WT RVFB, TGFβ1 stimulated both calcineurin and α-SMA mRNA expression, which was prevented in Eng+/− RVFB. In contrast, TGFβ1 induced calcineurin and α-SMA expression were increased in both WT and Eng+/−LVFB (FIGS. 4A-4C). To further explore the dependence of calcineurin expression on endoglin in RVFB and LVFB, cells were treated with TGFβ1 in the presence of increasing concentrations of the N-Eng Ab. TGFβ1 induced calcineurin and α-SMA protein expression were inhibited by the N-Eng Ab in RVFB not LVFB (FIG. 4D-4F). In contrast, TGFβ1 induced protein levels of pSmad-3 and pERK-1/2 were inhibited by N-Eng Ab treatment in both RVFB and LVFB (FIG. 3I-3J). These findings suggest that endoglin is required for TGFβ1-induced calcineurin expression and myofibroblast transformation of cardiac fibroblasts originating from the RV, not LV.

Previous studies of TGFβ1 activity in cardiac remodeling have focused on LV failure; yet, TGFβ1 signaling in the RV remains largely unexplored. The majority of understanding of the mechanisms governing RV remodeling stem primarily from data generated in models of LV failure. However, substantial differences between the RV and LV exist that support the potential for the two ventricles to have distinct responses to injury, including: (1) the developmental origin of the RV from a heart field distinct from the LV; (2) a thin RV free wall with susceptibility to increased wall stress; (3) a greater dependence of the RV stroke volume on afterload; and (4) enhanced RV contractile resilience to pressure overload. In this study, reduced endoglin expression had no effect on LV expression of calcineurin. Despite all that is known in the LV, regulation of profibrotic signaling in the RV remains poorly understood and the role of endoglin in the RV has never been studied. These studies exploring the role of endoglin in the RV response to pressure overload reveal that, although some similarities exist with the LV, there are also pathways unique to endoglin's role in the RV. Indeed, endoglin limited TGFβ1 signaling by Smad3 and ERK1/2 in both ventricles; however, in contrast to previous observations in the LV, endoglin is shown to regulate TGFβ1-induced calcineurin expression and activity in the RV. It was uniformly observed that reduced endoglin activity attenuated calcineurin expression and activity, as evidenced by reduced levels of downstream targets of calcineurin activity, including MYH7 and TRPC-6.

Figure 5B:
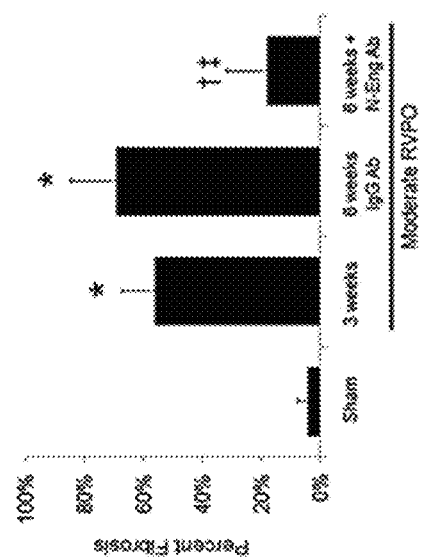
Figure 5A:
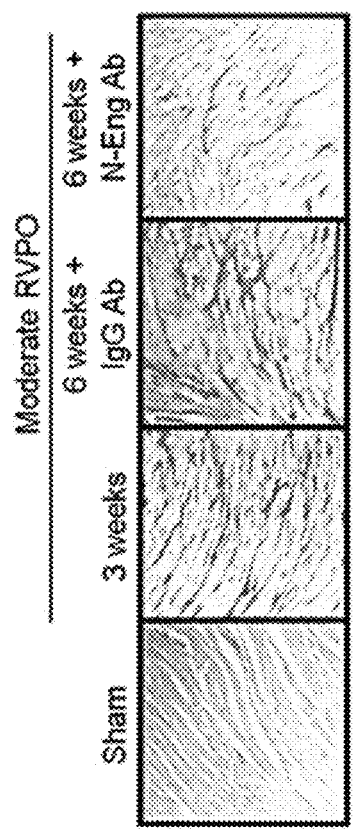
Figure 5C:
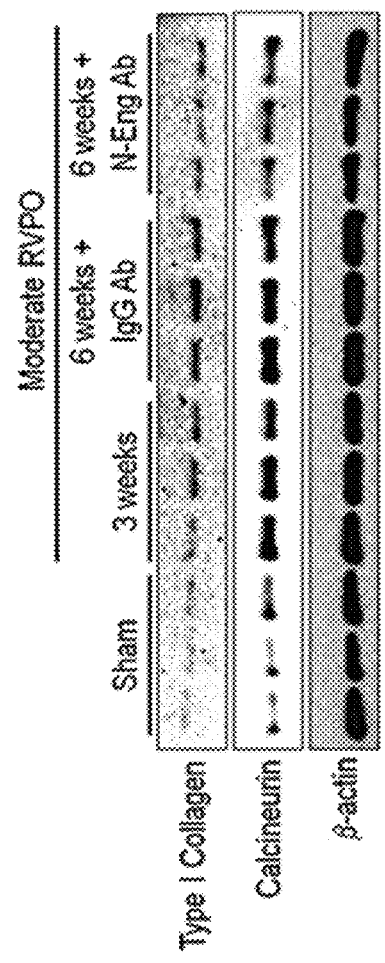
Figure 6:
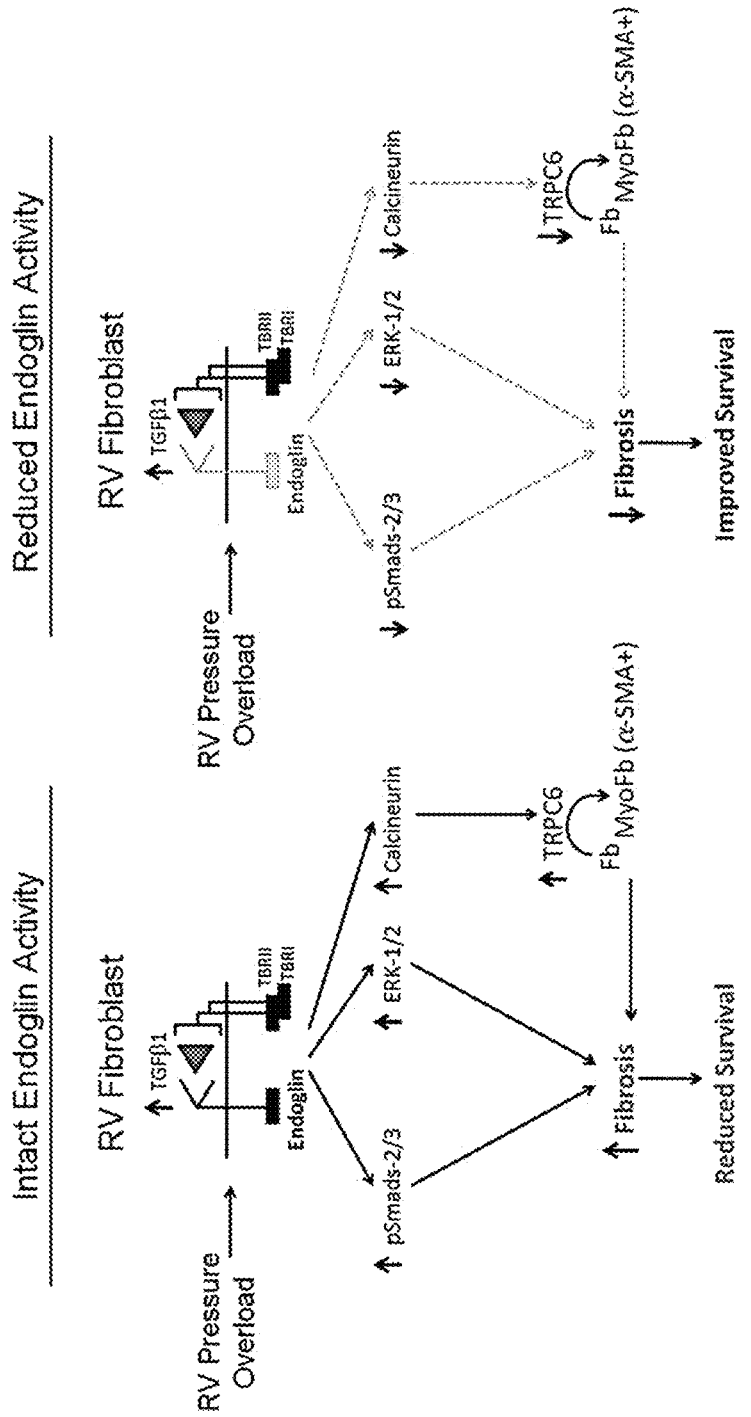
FIG. 6 shows that reduced endoglin activity limits TGFβ1-induced calcineurin expression and myofibroblast transformation in right ventricular fibroblasts. (Left panel) Endoglin RV promotes fibrosis by facilitating TGFβ1 signaling via canonical and non-canonical pathways including calcineurin-mediated myofibroblast transformation. (Right panel) Reduced endoglin activity in RVFB attenuates TGFβ1/calcineurin signaling and limits myofibroblast transformation and fibrosis, thereby improving survival.

Example 6: Neutralizing Endoglin Activity Reverses RV Fibrosis in Established RVPO To confirm the clinical utility of blocking endoglin activity as an approach to reduce cardiac fibrosis after established RVPO, WT mice subjected moderate RVPO for 3 weeks were randomized to receive either a N-Eng Ab or control IgG Ab for an additional 3 weeks. After 3 weeks of moderate RVPO, total body weight was reduced, while RV mass and systolic pressure were increased and RV stroke volume decreased compared to sham controls (Table 4). RV fibrosis, Type I collagen, and calcineurin expression were also increased compared to sham controls (FIG. 5). After an additional 3 weeks (6 weeks total) of moderate RVPO, both IgG and N-Eng Ab treated groups had persistently increased RV mass and RV systolic pressure with reduced cardiac output. No mortality was observed after moderate RVPO in either group at any time point (Table 4). RV fibrosis progressively worsened in mice treated with the control IgG Ab, but was significantly reduced in the N-Eng Ab treated group (FIG. 5). Type I collagen and calcineurin protein expression also increased progressively in the IgG group, but were reduced in the N-Eng Ab group. These findings confirm that blocking endoglin activity reverses RV fibrosis in chronic RVPO.

TABLE 4

Characterization of Chronic Right Ventricular Pressure Overload Induced by Moderate PAC in Wild-type mice treated with either a Neutralizing Antibody against Endoglin (N-Eng Ab) or IgG-Isotype Control Antibody (IgG Ab)

|  | PAC | | | |
| --- | --- | --- | --- | --- |
|  | Sham | 3 weeks | 6 weeks + IgG Ab | 6 weeks + N-Eng Ab |
| Total body weight, g | 31 ± 1 | 27 ± 2* | 27 ± 1* | 27 ± 2* |
| RV weight/tibial length, g/mm | 1.4 ± 0.5 | 2.7 ± 0.5* | 2.7 ± 0.4* | 2.5 ± 0.4* |
| LV weight/tibial length, g/mm | 5.4 ± 0.5 | 3.5 ± 0.1* | 4.1 ± 0.1* | 4.5 ± 0.2* |
| Hemodynamic variables | | | | |
| RV systolic pressure, mm Hg | 26 ± 1 | 70 ± 5* | 69 ± 10* | 69 ± 14* |
| RV end-diastolic pressure, mm Hg | 1 ± 1 | 4 ± 2 | 2 ± 1 | 2 ± 1 |
| RV +dp/dt, mm Hg/sec | 2212 ± 52 | 4836 ± 929* | 4215 ± 674* | 4072 ± 875* |
| RV −dp/dt, mm Hg/sec | 2115 ± 64 | 4171 ± 278* | 4345 ± 818* | 3916 ± 875* |
| RV stroke volume, μL | 9 ± 2 | 3 ± 1* | 3 ± 2 | 3 ± 2* |
| Cardiac output, mL/min | 4.3 ± 1 | 1.5 ± 1* | 1.3 ± 0.5* | 1.4 ± 0.6* |
| Heart rate, beats per min | 500 ± 81 | 592 ± 83 | 527 ± 69 | 550 ± 52 |

PAC indicates pulmonary artery constriction; LV, left ventricular; RV, right ventricular.
*$P < 0.01$ versus sham (n = 6/group).

Figure 8A:
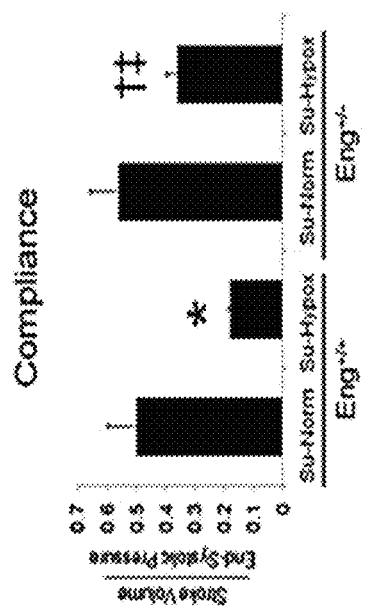
FIGS. 8A-8I show reduced endoglin expression limits fibrosis and calcineurin expression in a murin model of angio-obliterative pulmonary hypertension.
Figure 8B:
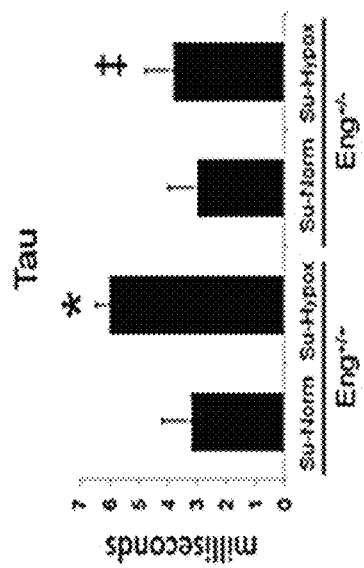
Figure 8C:
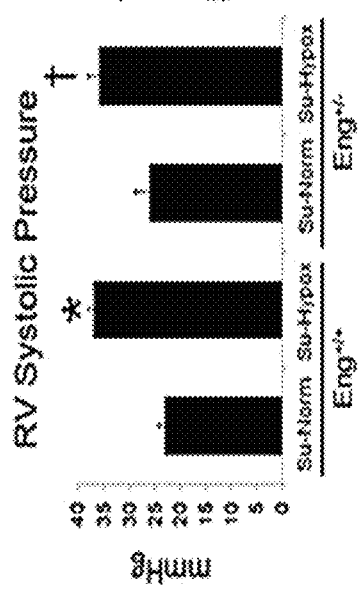
Figures 8D, 8E, 8F:
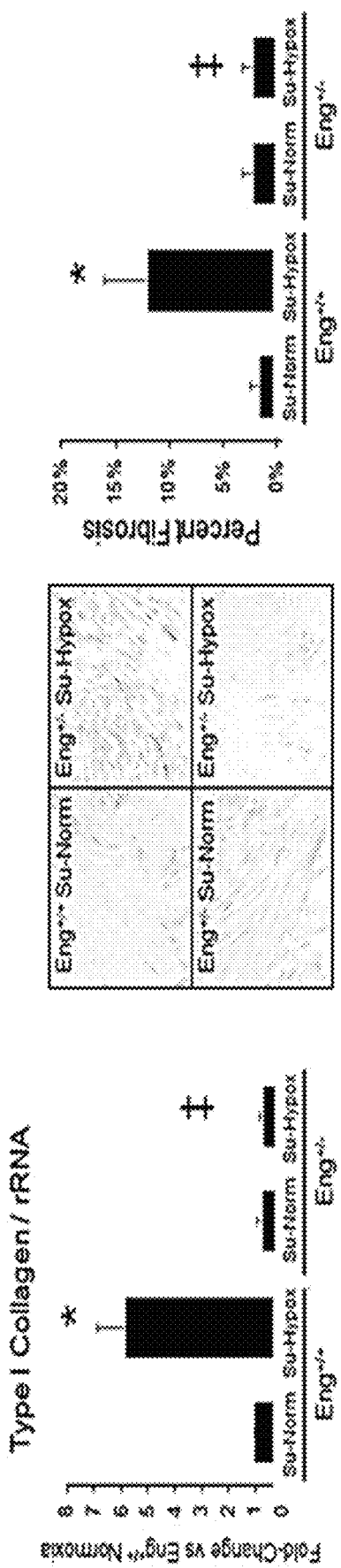
Figure 8G:
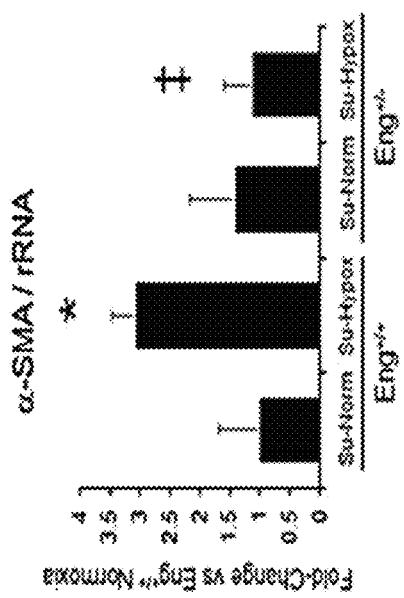
Figure 8H:
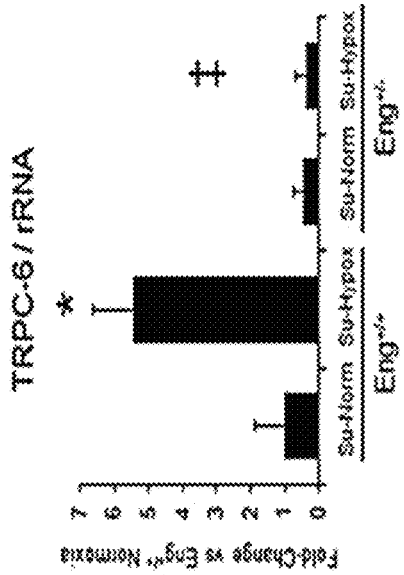
Figure 8I:
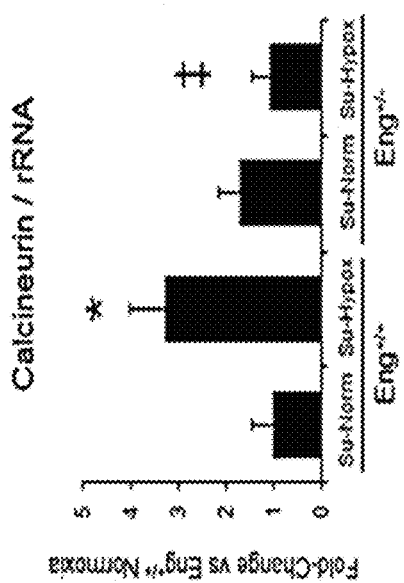

Example 7: Reduced Endoglin Expression Preserves RV Function and Limits RV Fibrosis in a Model of Angio-Obliterative Pulmonary Hypertension To further explore a functional role for endoglin in RV remodeling, the well-established model of angio-obliterative pulmonary hypertension induced by exposure to hypoxia and the anti-vascular endothelial growth factor compound, Sugen, was studied in WT, compared to Eng+/− mice. All mice survived treatment with Sugen+Hypoxia for 5 weeks, and no significant change in total body weight, RV or LV weights, RV stroke volume, or cardiac output was observed between groups (Table 2). Increased RV systolic pressure (RVSP) was observed in both WT and Eng+/− mice after 5 weeks of exposure to Sugen+ Hypoxia (FIG. 8A). No difference in RV dP/dtmax was observed between WT and Eng+/− groups treated with Sugen+ Hypoxia, demonstrating a similar response to RVPO in both types of mice. WT mice exposed to Sugen+ hypoxia developed evidence of abnormal diastolic RV function, including increased Tau (a measure of instantaneous isovolumic relaxation) and decreased RV compliance (FIGS. 8B and 8C), whereas Eng+/− mice demonstrated no change in Tau and relatively preserved RV compliance. To explore the mechanism for the differences in RV diastolic function, RV fibrosis and calcineurin signaling were examined. Exposure to Sugen+Hypoxia increased type I collagen mRNA expression and histologic levels of collagen abundance in WT, not Eng+/−, mice (FIG. 8D through 8F). Calcineurin, TRPC-6, and α-SMA mRNA levels were increased by Sugen+ Hypoxia in WT, not Eng+/−, mice (FIG. 8G through 8I). These findings suggest that, despite identical degrees of RVPO, reduced endoglin expression in Eng+/− mice preserved indices of RV diastolic function, limited RV collagen accumulation, attenuated up-regulation of calcineurin and TRPC-6, and limited myofibroblast transformation in the RV.

Example 8: Endoglin Selectively Modulates TRP Channel Expression in Response to LV or RV Pressure Overload To explore a functional role for endoglin as a regulator of TRPC expression in response to RV or LV pressure overload, Eng+/− and Eng+/+ mice were exposed to TAC or PAC constriction for 10 weeks. Biventricular tissue was then analyzed by RT-PCR.

Figure 10A:
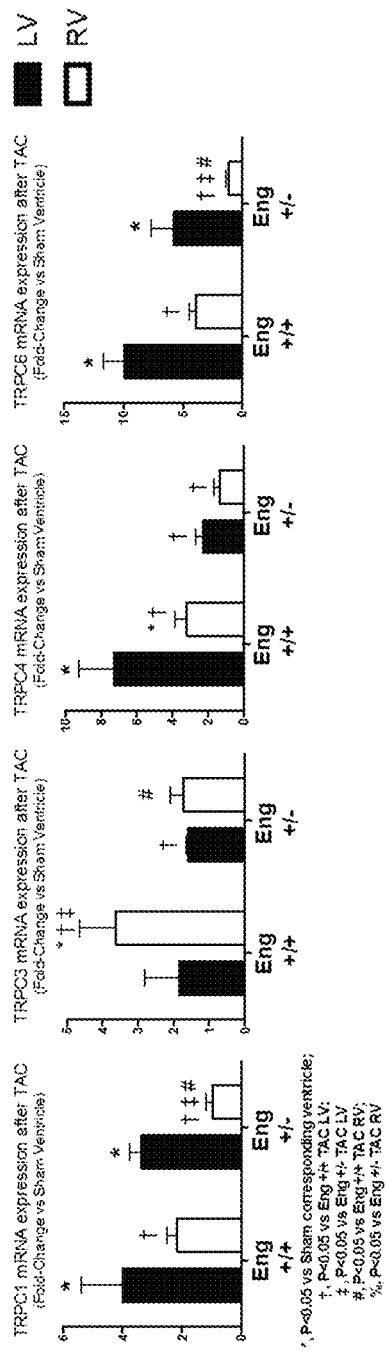
FIGS. 10A-10B show RV and LV levels of TRPC1, TRPC3, TRPC4, and TRPC6 in Eng+/+ and Eng+/− mice after exposure to TAC (FIG. 10A) and PAC (FIG. 10B) for 10 weeks.
Figure 10B:
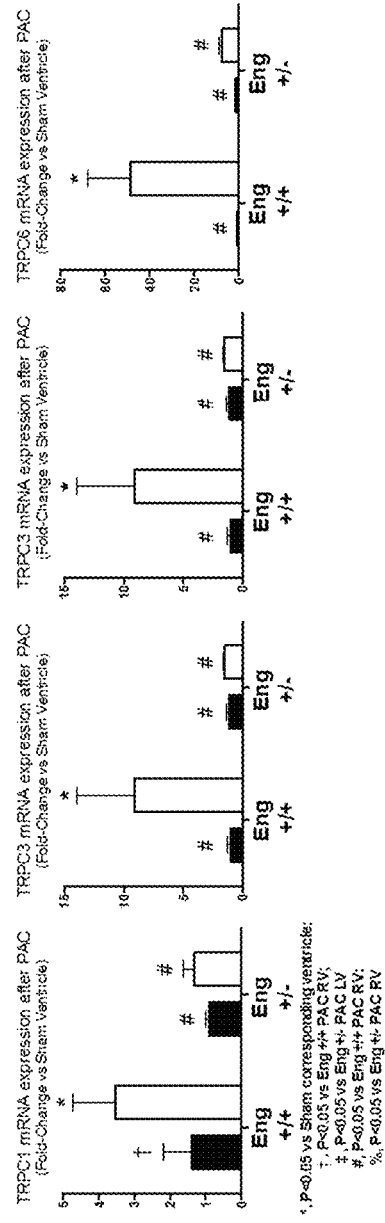
Figure 11A:
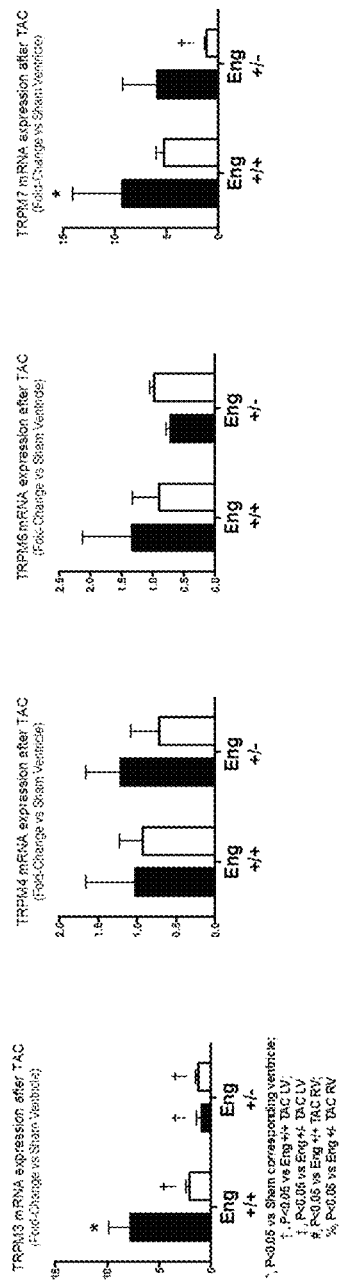
FIGS. 11A-11B show RV and LV levels of TRPM3, TRPM5, TRPM6, and TRPM7 in Eng+/+ and Eng+/− mice after exposure to TAC (FIG. 11A) and PAC (FIG. 11B) for 10 weeks.
Figure 11B:
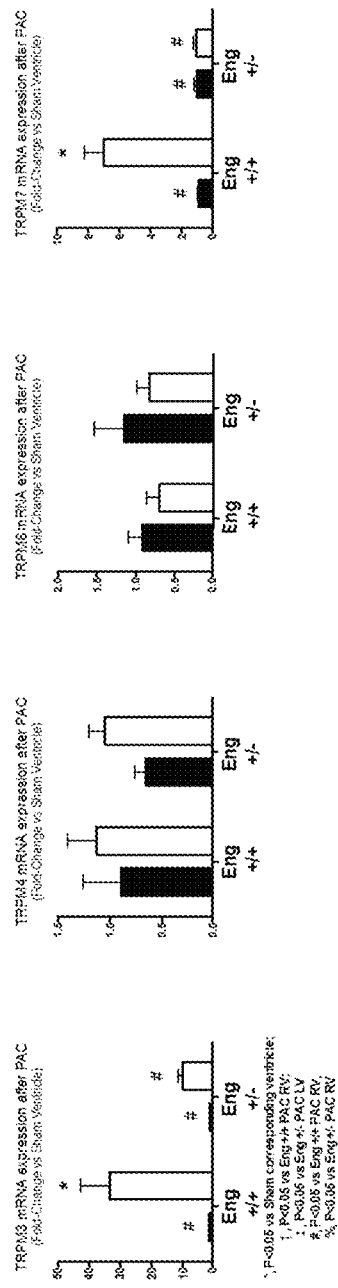
Figure 12A:
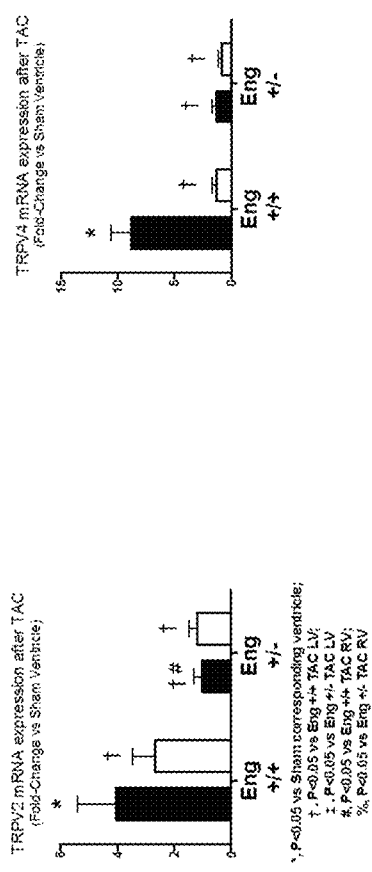
FIGS. 12A-12B show RV and LV levels of TRPV2 and TRPV4 in Eng+/+ and Eng+/− mice after exposure to TAC (FIG. 12A) and PAC (FIG. 12B) for 10 weeks.
Figure 12B:
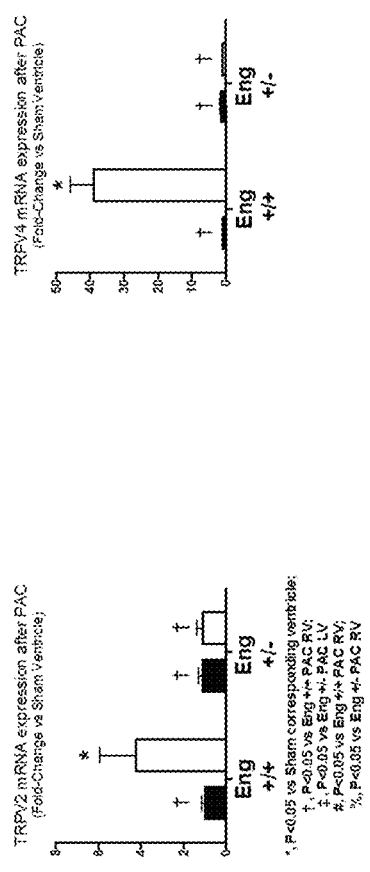

After TAC, LV levels of TPRC1 and 6 were increased in both Eng+/+ and Eng+/− mice compared to sham controls. LV levels of TRPC4 were increased in Eng+/+, not Eng+/− mice after TAC (FIG. 10A). After PAC, RV levels of TRPC 1, 3, 4, and 6 were increased in Eng+/+ compared to sham controls. In contrast, chronic RV pressure overload did not increase RV levels of TRPC 1,3,4, and 6 in Eng+/− mice compared to sham controls (FIG. 10B). After TAC, LV levels of TRPM3 and 7 were increased in Eng+/+ compared to sham controls (FIG. 11A). After PAC, RV levels of TRM3 and 7 were increased in Eng+/+ compared to sham controls (FIG. 11B). In contrast, chronic RV pressure overload did not increase RV levels of TRPM3 and 7 in Eng+/− mice compared to sham controls (FIG. 11B). After TAC, LV levels of TRPV2 and 4 were increased in Eng+/+, not Eng+/− mice after TAC (FIG. 12A). After PAC, RV levels of TRPV2 and 4 were increased in Eng+/+ compared to sham controls. In contrast, chronic RV pressure overload did not increase RV levels of TRPV2 and 4 in Eng+/− mice compared to sham controls (FIG. 12B).

The TRPC family of Ca2+ permeable channels includes 7 members and can increase intracellular calcium levels ([Ca2+]i), which activates calcineurin expression in fibroblasts and promotes myofibroblast transformation. Several previous reports have established that TRPC-6 amplifies pathological signaling by participating in a self-propagating feed-forward circuit mediated by calcineurin activity and is therefore a potentially important target of therapy in cardiac remodeling (Kuwahara et al., *J Clin Invest.* 116:3114-3126, 2006; Davis et al., *Dev Cell.* 23:705-715, 2012; and Berry et al., *Circ Res.* 109:407-417, 2011). Until now, no studies have examined the functional role of endoglin and TRP signaling pathways in RVPO. Taken together, the data show that pressure overload induces distinct profiles of TRP expression in the RV and LV of mice and in some cases, expression of particular TRP channels specifically in the RV require full endoglin activity.

Figure 13:
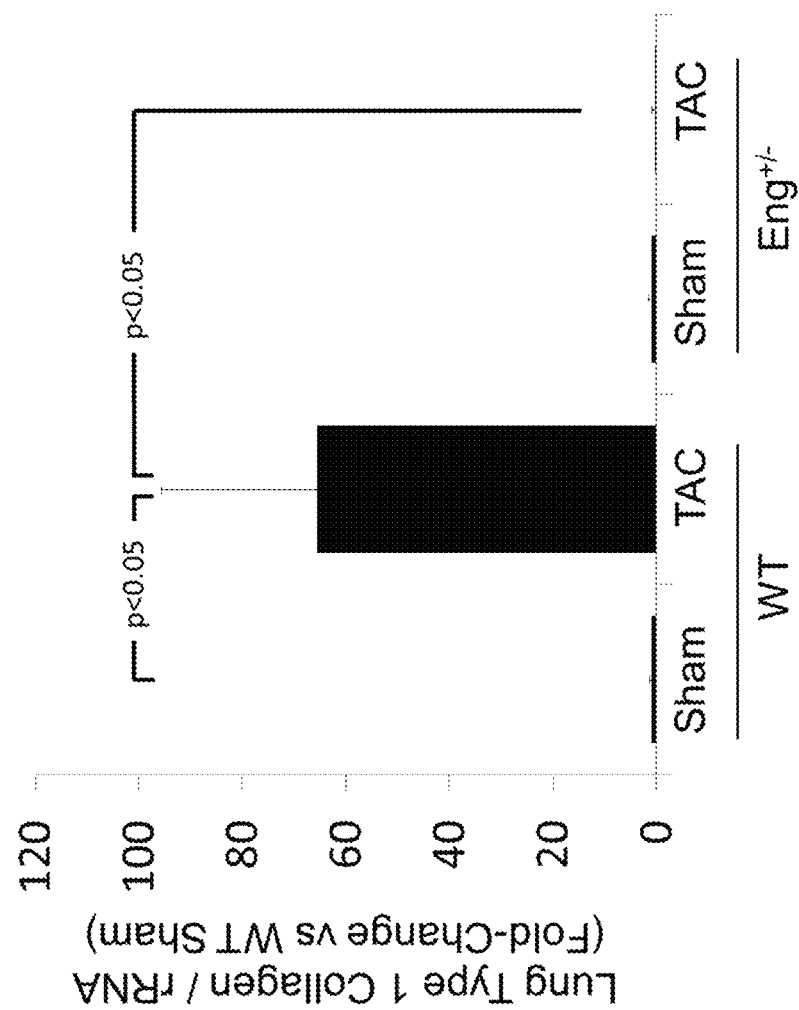
FIG. 13 is a graph showing lung type I collagen expression in Eng+/+ and Eng+/− mice after exposure to TAC.

Example 9: Endoglin is Required for Regulation of Fibrotic Signaling in the Lung and Kidney To determine whether endoglin is an important component in fibrotic signaling, not limited to the RV, fibrotic signaling in lung tissue was examined in the context of Eng+/+ and Eng+/− mice. FIG. 13 shows that endoglin is required for collagen expression in mouse lung tissue. The PCR result was obtained in mice subjected to two weeks of pulmonary venous congestion due to thoracic aortic constriction (TAC) and left heart failure. The results show that reduced endoglin expression attenuates increased collagen expression in lung tissue.

In addition, fibrotic signaling in renal tissue was examined in the context of Eng+/+ and Eng+/− mice. FIG. 14A shows that endoglin is required for collagen expression in mouse renal tissue. The PCR result was obtained in mice induced with LV failure by TAC. The results show that reduced endoglin expression decreases collagen expression in renal tissue. Plasminogen activator inhibitor-1 (PAI-1) expression was also analyzed in renal tissue. PAI-1 is an inhibitor of serin proteases tPA and uPA/urokinase and thus is involved in the regulation of fibrinolysis. Excess levels of PAI-1 has been implicated in metabolic syndrome and various other disease states (e.g., atherothrombosis, obesity, and various forms of cancer). FIG. 14B shows that endoglin is required for PAI-1 expression in mouse renal tissue and that reduced endoglin expression decreases PAI-1 expression in renal tissue. Thus, together, the data indicate that endoglin is required for regulation of fibrotic signaling and modulation of endoglin activity would be useful in reducing fibrosis in the context of treating lung disease and kidney disease.

The central findings in these studies is that endoglin modulates TGFβ1 signaling through canonical, noncanonical, and calcineurin-mediated pathways in the RV, modulates fibrotic signaling in organs, such as the lung or kidney, presumably also through TGFβ1 signaling, and could be a therapeutic target to limit organ fibrosis and improve survival in diseases characterized by RVPO and/or fibrosis. Several findings reported herein include: (1) Endoglin is necessary for TGFβ1-induced increase in expression of TRPC-6 and α-SMA by a calcineurin-dependent mechanism in human RV fibroblasts; (2) TRPC-6 mediates a feedback loop promoting calcineurin expression and myofibroblast transformation in human RV fibroblasts that is also dependent on endoglin; (3) in Eng+/− mice exposed to Sugen+ Hypoxia, reduced endoglin activity improved RV diastolic function, limited fibrosis, and attenuated expression of calcineurin, TRPC-6, and α-SMA; (4) in the most severe model of surgical pressure overload, reduced endoglin activity, induced either by genetic means or by treatment with a neutralizing Ab, improved survival, reduced RV fibrosis, and limited TGFβ1 signaling through canonical, noncanonical, and calcineurin-mediated pathways in the RV; (5) in mice with established RV fibrosis, neutralizing endoglin activity reversed RV fibrosis and attenuated expression of both type I collagen and calcineurin and (6) reduced endoglin expression in the lung and kidney of mice induced with heart failure attenuates increased collagen expression and decreases key regulators of fibrinolysis. Given the importance of calcineurin and TRPC-6 in adaptive and maladaptive cardiac remodeling, these findings identify endoglin as a regulator of TGFβ1-signaling cascades involved in RV remodeling and further show that targeting endoglin activity improves RV function in heart failure, lung disease, and/or kidney disease. Because endoglin plays a critical role in TGFβ1 signaling, targeting endoglin activity also provides a method for controlling pathological wound healing and preventing fibrosis related morbidity and mortality in organs generally. Accordingly, endoglin can serve as a therapeutic target to limit organ fibrosis and improve survival in disease states characterized by RVPO and/or fibrosis.

Other Embodiments

All patents, patent applications, and publications mentioned in this specification are herein incorporated by reference to the same extent as if each independent patent, patent application, or publication was specifically and individually indicated to be incorporated by reference.

The invention claimed is:

1. A method of treating a fibrotic disease in a human subject in need thereof, the method comprising administering to the subject a therapeutically effective amount of an interfering ribonucleic acid (RNA) that is specific for Endoglin mRNA and that reduces Endoglin expression, wherein the fibrotic disease is selected from the group consisting of lung fibrosis, kidney fibrosis, and liver fibrosis.

2. The method of claim 1, wherein the interfering RNA is administered in combination with an antifibrotic agent.

3. The method of claim 2, wherein the antifibrotic agent is selected from the group consisting of: pentoxyphiline, tocopherol, vitamin E, pioglitazone, INT 747, peginterferon 2b, infliximab, ribavirin, glycyrrhizin, candesartan, losartan, irbesartan, ambrisentan, FG-3019, warfarin, insulin, colchicines, peginterferon 2a, etanercept, pirfenidone, nintedanib, and IL-10.

4. The method of claim 1, wherein the fibrotic disease is lung fibrosis and the subject has interstitial lung disease.

5. The method of claim 1, wherein the fibrotic disease is kidney fibrosis and the subject has diabetic nephropathy.

6. The method of claim 1, wherein the fibrotic disease is liver fibrosis and the subject has nonalcoholic steatohepatitis (NASH).

7. The method of claim 1, wherein the lung fibrosis is idiopathic pulmonary fibrosis.

8. The method of claim 1, wherein the interfering RNA is an siRNA.

9. The method of claim 8, wherein the siRNA comprises a strand having a length of from 21 nucleotides to 23 nucleotides.

10. The method of claim 8, wherein the siRNA is completely complementary to at least 18 consecutive nucleotides of an Endoglin mRNA.

* * * * *

SEQUENCE LISTING

```
<160> NUMBER OF SEQ ID NOS: 22

<210> SEQ ID NO 1
<211> LENGTH: 582
<212> TYPE: PRT
<213> ORGANISM: Homo sapiens

<400> SEQUENCE: 1

Met Ser Pro Ala Pro Arg Pro Arg Cys Leu Leu Pro Leu Leu
1               5                   10                  15

Thr Leu Gly Thr Ala Leu Ala Ser Leu Gly Ser Ala Gln Ser Ser Ser
                20                  25                  30

Phe Ser Pro Glu Ala Trp Leu Gln Gln Tyr Gly Tyr Leu Pro Pro Gly
            35                  40                  45

Asp Leu Arg Thr His Thr Gln Arg Ser Pro Gln Ser Leu Ser Ala Ala
        50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255
```

```
Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
        435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Glu Thr Glu Val Ile Ile Ile Glu
        515                 520                 525

Val Asp Glu Glu Gly Gly Gly Ala Val Ser Ala Ala Ala Val Val Leu
    530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
            580

<210> SEQ ID NO 2
<211> LENGTH: 176
<212> TYPE: PRT
<213> ORGANISM: Homo sapiens

<400> SEQUENCE: 2

Ala Ile Gln Gly Leu Lys Trp Gln His Asn Glu Ile Thr Phe Cys Ile
1               5                   10                  15

Gln Asn Tyr Thr Pro Lys Val Gly Glu Tyr Ala Thr Tyr Glu Ala Ile
            20                  25                  30

Arg Lys Ala Phe Arg Val Trp Glu Ser Ala Thr Pro Leu Arg Phe Arg
        35                  40                  45
```

```
Glu Val Pro Tyr Ala Tyr Ile Arg Glu Gly His Glu Lys Gln Ala Asp
 50                  55                  60
Ile Met Ile Phe Phe Ala Glu Gly Phe His Gly Asp Ser Thr Pro Phe
 65                  70                  75                  80
Asp Gly Glu Gly Gly Phe Leu Ala His Ala Tyr Phe Pro Gly Pro Asn
                 85                  90                  95
Ile Gly Gly Asp Thr His Phe Asp Ser Ala Glu Pro Trp Thr Val Arg
                100                 105                 110
Asn Glu Asp Leu Asn Gly Asn Asp Ile Phe Leu Val Ala Val His Glu
                115                 120                 125
Leu Gly His Ala Leu Gly Leu Glu His Ser Ser Asp Pro Ser Ala Ile
                130                 135                 140
Met Ala Pro Phe Tyr Gln Trp Met Asp Thr Glu Asn Phe Val Leu Pro
145                 150                 155                 160
Asp Asp Asp Arg Arg Gly Ile Gln Gln Leu Tyr Gly Gly Glu Ser Gly
                165                 170                 175

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
aagggtccct ctggagaacc                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
tctagagcca gggagaccca                                           20

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ccacagggat gttgcctagt g                                         21

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
gtcccgtggt tctcagtggt a                                         21

<210> SEQ ID NO 7
<211> LENGTH: 20
<212> TYPE: DNA
<213> ORGANISM: Artificial Sequence
<220> FEATURE:
```

<223> OTHER INFORMATION: Synthetic Construct

<400> SEQUENCE: 7
ctgccaatgc tgtgcgtgaa                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gctggagtcg taggccaagt                                                   20

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct

<400> SEQUENCE: 9
gcatccacga aaccaccta                                                    19

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
cacgagtaac aaatcaaagc                                                   20

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct

<400> SEQUENCE: 11
atgtgccgga ccttggaa                                                     18

<210> SEQ ID NO 12
<211> LENGTH: 22
<212> TYPE: DNA
<213> ORGANISM: Artificial Sequence
<220> FEATURE:
<223> OTHER INFORMATION: Synthetic Construct

<400> SEQUENCE: 12
cctcgggtta gctgagagat ca                                                22

<210> SEQ ID NO 13
<211> LENGTH: 19
<212> TYPE: DNA
<213> ORGANISM: Artificial Sequence
<220> FEATURE:
<223> OTHER INFORMATION: Synthetic Construct

<400> SEQUENCE: 13
ggcggctctc taaaggctg                                                    19

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct

<400> SEQUENCE: 14
tggggtagta gccatacggt g                    21

<210> SEQ ID NO 15
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15
gtcgagggcc aagacgaag                       19

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16
cagatcacgt catcgcacaa c                    21

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
tgcatcaatt cttcgacagg                      20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
aaggcccaca aatacagcac                      20

<210> SEQ ID NO 19
<211> LENGTH: 19
<212> TYPE: DNA
<213> ORGANISM: Artificial Sequence
<220> FEATURE:
<223> OTHER INFORMATION: Synthetic Construct

<400> SEQUENCE: 19
ccgaccgaat gcagaagga                       19

<210> SEQ ID NO 20
<211> LENGTH: 21
<212> TYPE: DNA
<213> ORGANISM: Artificial Sequence
<220> FEATURE:
<223> OTHER INFORMATION: Synthetic Construct -continued

```
<400> SEQUENCE: 20
acagagtatt tgcgctccga a                                              21

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
gccaatgagc atctggaaat                                                20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
tggagtcaca tcatgggaga                                                20
```